(12) United States Patent
Messerly

(10) Patent No.: US 6,976,969 B2
(45) Date of Patent: Dec. 20, 2005

(54) BLADES WITH FUNCTIONAL BALANCE ASYMMETRIES FOR USE WITH ULTRASONIC SURGICAL INSTRUMENTS

(75) Inventor: Jeffrey D. Messerly, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 230 days.

(21) Appl. No.: 10/047,601

(22) Filed: Jan. 14, 2002

(65) Prior Publication Data

US 2002/0143355 A1 Oct. 3, 2002

Related U.S. Application Data

(63) Continuation of application No. 09/957,174, filed on Sep. 20, 2001, which is a continuation of application No. 09/412,257, filed on Oct. 5, 1999, now Pat. No. 6,325,811.

(51) Int. Cl.$^7$ .................................................. A61B 1/00
(52) U.S. Cl. ........................... 601/2; 600/461; 606/169; 604/22
(58) Field of Search .................................. 600/437–472; 601/1, 2–4; 604/22; 606/1, 169, 171, 204

(56) References Cited

U.S. PATENT DOCUMENTS

| | | |
|---|---|---|
| 2,990,616 A | 7/1961 | Balamuth et al. |
| 3,053,124 A | 11/1962 | Balamuth et al. |
| 3,404,677 A | 10/1968 | Springer |
| 3,433,226 A | 3/1969 | Boyd |
| 3,526,219 A | 9/1970 | Balamuth |
| 3,636,943 A | 1/1972 | Balamuth |
| 3,830,240 A | 8/1974 | Anteonevich et al. |
| 3,861,391 A | 1/1975 | Anteonevich et al. |
| 3,862,630 A | 1/1975 | Balamuth |
| 3,990,452 A | 11/1976 | Murry et al. |
| 4,136,700 A | 1/1979 | Broadwin et al. |
| 4,169,984 A | 10/1979 | Parisi |
| 4,526,571 A | 7/1985 | Wukchinich |

(Continued)

FOREIGN PATENT DOCUMENTS

| | | |
|---|---|---|
| DD | 203229 | 10/1983 |
| EP | 0 830 845 A1 | 9/1996 |
| EP | 0968684 A1 | 1/2000 |
| SU | 452338 A | 12/1974 |
| WO | WO 98/14126 | 4/1998 |

OTHER PUBLICATIONS

EPO Search Report dated Aug. 3, 2004 for related patent application 09/412,257, European Patent Application No. 00 96 1666.

International Standard IEC 61847 Ultrasonic—Surgical systems—"Measurement and declaration of the basic output characteristics" © IEC 1998 Droits de reproduction reserves.

*Primary Examiner*—Brian L. Casler
*Assistant Examiner*—William Jung

(57) ABSTRACT

Disclosed is an ultrasonic surgical instrument that combines end-effector geometry to best affect the multiple functions of a shears-type configuration. The shape of the blade is characterized by a radiused cut offset by some distance to form a curved geometry. The cut creates a curved surface with multiple asymmetries causing multiple imbalances within the blade. Imbalance due to the curve of the instrument is corrected by a non-functional asymmetry proximal to the functional asymmetry. Imbalance due to the asymmetric cross-section of the blade is corrected by the appropriate selection of the volume and location of material removed from a functional asymmetry. The shape of the blade in one embodiment of the present invention is characterized by two radiused cuts offset by some distance to form a curved and potentially tapered geometry. These two cuts create curved surfaces including a concave surface and a convex surface. The length of the radiused cuts affects, in part, the acoustic balancing of the transverse motion induced by the curved shape.

10 Claims, 17 Drawing Sheets

U.S. PATENT DOCUMENTS

| | | | |
|---|---|---|---|
| 4,634,419 A | 1/1987 | Kreizman et al. | |
| 4,911,161 A | 3/1990 | Schnechter | |
| 4,920,954 A | 5/1990 | Alliger et al. | |
| 4,974,581 A | 12/1990 | Wiksell | |
| 4,992,048 A | 2/1991 | Goof | |
| 5,019,083 A | 5/1991 | Klapper et al. | |
| 5,047,008 A | 9/1991 | de Juan, Jr. et al. | |
| 5,047,043 A | 9/1991 | Kubota et al. | |
| 5,057,119 A | 10/1991 | Clark et al. | |
| 5,059,210 A | 10/1991 | Clark et al. | |
| 5,180,363 A | 1/1993 | Idemoto et al. | |
| 5,188,102 A | 2/1993 | Idemoto et al. | |
| 5,205,817 A | 4/1993 | Idemoto et al. | |
| 5,221,282 A | 6/1993 | Wuchchinich | |
| 5,222,937 A | 6/1993 | Kagawa | |
| D339,419 S | 9/1993 | Hood et al. | |
| 5,248,296 A | 9/1993 | Alliger | |
| 5,263,957 A | 11/1993 | Davison | |
| D344,799 S | 3/1994 | Hood et al. | |
| D345,794 S | 4/1994 | Hood et al. | |
| 5,312,329 A | 5/1994 | Beaty et al. | |
| 5,318,570 A | 6/1994 | Hood et al. | |
| 5,322,055 A | 6/1994 | Davison et al. | |
| 5,324,297 A | 6/1994 | Hood et al. | |
| 5,324,299 A | 6/1994 | Davison et al. | |
| 5,346,502 A | 9/1994 | Estabrook et al. | |
| 5,397,293 A | 3/1995 | Alliger et al. | |
| 5,413,578 A | 5/1995 | Zahedi | |
| 5,417,654 A | 5/1995 | Kelman | |
| 5,449,370 A | 9/1995 | Vaitekunas | |
| 5,480,379 A | 1/1996 | LaRosa | |
| 5,489,292 A | 2/1996 | Tovey et al. | |
| 5,509,922 A | 4/1996 | Aranyi et al. | |
| 5,531,597 A | 7/1996 | Foulkes et al. | |
| 5,630,420 A | 5/1997 | Vaitekunas | |
| 5,653,724 A | 8/1997 | Imonti | |
| 5,669,922 A | 9/1997 | Hood | |
| 5,676,649 A | 10/1997 | Boukhny et al. | |
| 5,776,155 A | 7/1998 | Beaupre et al. | |
| 5,873,873 A * | 2/1999 | Smith et al. | 606/1 |
| 5,893,835 A | 4/1999 | Witt et al. | |
| 5,897,523 A * | 4/1999 | Wright et al. | 604/22 |
| 5,935,142 A | 8/1999 | Hood | |
| 5,935,144 A | 8/1999 | Estabrook | |
| 5,938,633 A | 8/1999 | Beaupre | |
| 5,944,737 A | 8/1999 | Tsonton et al. | |
| 5,947,593 A | 9/1999 | Inoue et al. | |
| 5,947,984 A * | 9/1999 | Whipple | 606/151 |
| 5,954,736 A * | 9/1999 | Bishop et al. | 606/157 |
| 5,980,510 A * | 11/1999 | Tsonton et al. | 606/1 |
| 6,024,750 A * | 2/2000 | Mastri et al. | 606/169 |
| 6,036,667 A * | 3/2000 | Manna et al. | 604/22 |
| 6,051,010 A | 4/2000 | DiMatteo et al. | |
| 6,056,735 A * | 5/2000 | Okada et al. | 606/1 |
| 6,063,050 A | 5/2000 | Manna et al. | |
| 6,068,647 A * | 5/2000 | Witt et al. | 606/205 |
| 6,090,120 A | 7/2000 | Wright et al. | |
| 6,117,152 A | 9/2000 | Huitema | |
| 6,254,623 B1 * | 7/2001 | Haibel et al. | 606/169 |
| 6,283,981 B1 * | 9/2001 | Beaupre | 606/169 |
| 6,325,811 B1 * | 12/2001 | Messerly | 606/169 |
| 6,454,781 B1 * | 9/2002 | Witt et al. | 606/169 |

* cited by examiner

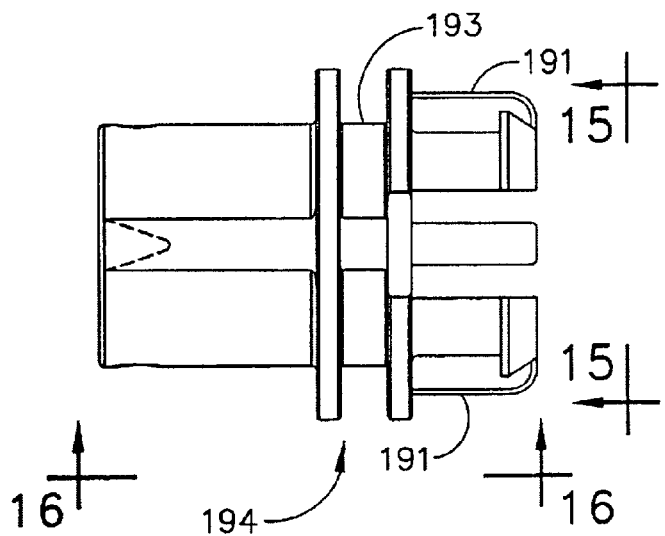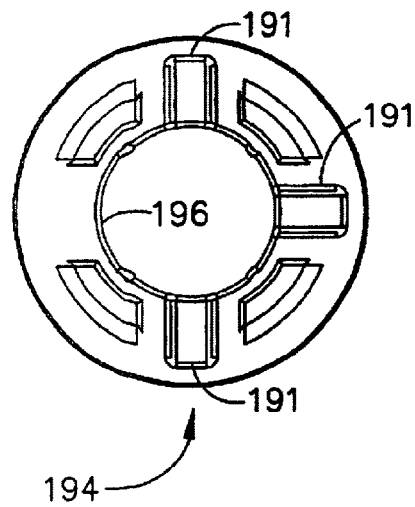
FIG. 14  FIG. 15
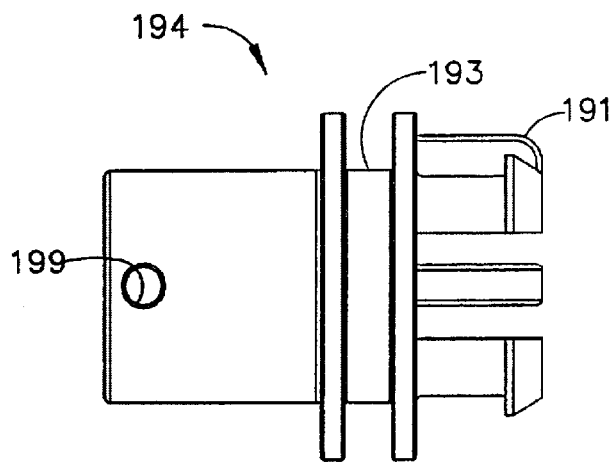
FIG. 16

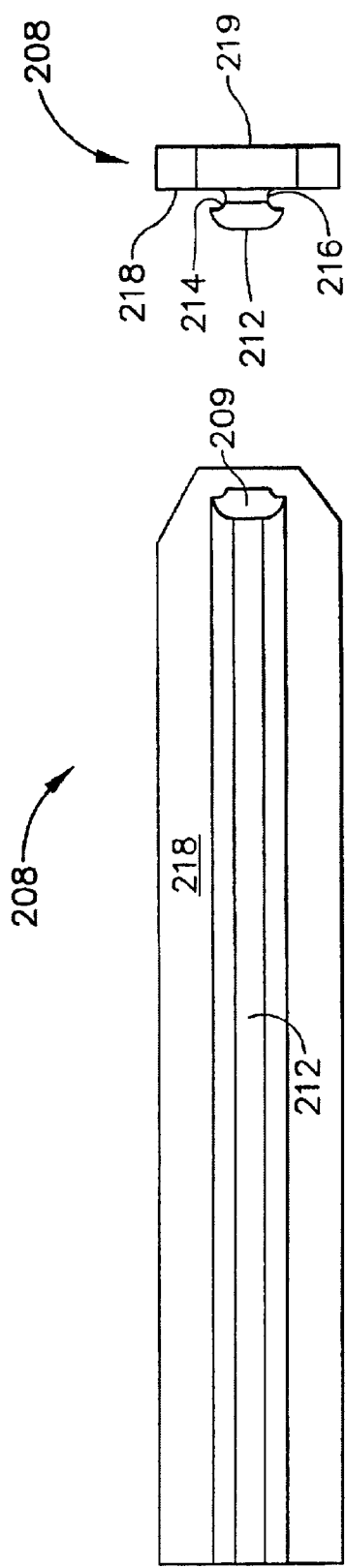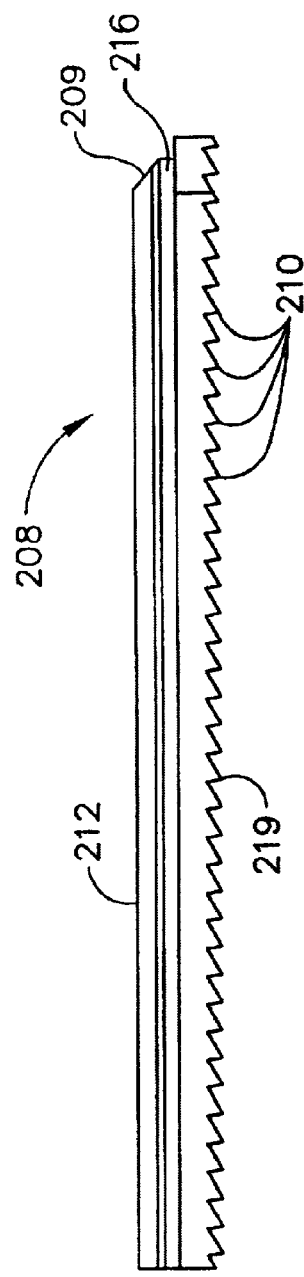

BLADES WITH FUNCTIONAL BALANCE ASYMMETRIES FOR USE WITH ULTRASONIC SURGICAL INSTRUMENTS

CROSS REFERENCE TO RELATED PATENT APPLICATIONS

This is a continuation of U.S. patent application Ser. No. 09/957,174, filed on Sep. 20, 2001, which is a continuation of U.S. patent application Ser. No. 09/412,257, filed on Oct. 5, 1999, now U.S. Pat. No. 6,325,811 B1.

FIELD OF THE INVENTION

The present invention relates, in general, to ultrasonic surgical instruments and, more particularly, to multifunctional curved blades with functional asymmetries for use with ultrasonic surgical instruments to minimize undesirable motion.

BACKGROUND OF THE INVENTION

This application is related to the following copending patent applications: application Ser. No. 08/948,625 filed Oct. 10, 1997; application Ser. No. 08/949,133 filed Oct. 10, 1997; application Ser. No. 09/106,686 filed Jun. 29, 1998; application Ser. No. 09/337,077 filed Jun. 21, 1999; application Ser. No. 09/412,557 filed Oct. 5, 1999, which issued as U.S. Pat. No. 6,325,811B1; application Ser. No. 09/412,996; filed Oct. 5, 1999; application Ser. No. 09/413,225 filed Oct. 5, 1999; and Ser. No. 09/957,174 filed Sep. 20, 2001 which are hereby incorporated herein by reference.

Ultrasonic instruments, including both hollow core and solid core instruments, are used for the safe and effective treatment of many medical conditions. Ultrasonic instruments, and particularly solid core ultrasonic instruments, are advantageous because they may be used to cut and/or coagulate organic tissue using energy in the form of mechanical vibrations transmitted to a surgical end-effector at ultrasonic frequencies. Ultrasonic vibrations, when transmitted to organic tissue at suitable energy levels and using a suitable end-effector, may be used to cut, dissect, or cauterize tissue. Ultrasonic instruments utilizing solid core technology are particularly advantageous because of the amount of ultrasonic energy that may be transmitted from the ultrasonic transducer through the waveguide to the surgical end-effector. Such instruments are particularly suited for use in minimally invasive procedures, such as endoscopic or laparoscopic procedures, wherein the end-effector is passed through a trocar to reach the surgical site.

Ultrasonic vibration is induced in the surgical end-effector by, for example, electrically exciting a transducer which may be constructed of one or more piezoelectric or magnetostrictive elements in the instrument hand piece. Vibrations generated by the transducer section are transmitted to the surgical end-effector via an ultrasonic waveguide extending from the transducer section to the surgical end-effector. The waveguides and end-effectors are designed to resonate at the same frequency as the transducer. Therefore, when an end-effector is attached to a transducer the overall system frequency is still the same frequency as the transducer itself.

The amplitude of the longitudinal ultrasonic vibration at the tip, d, behaves as a simple sinusoid at the resonant frequency as given by:

$$d = A \sin(\omega t) \quad \text{(equation 1)}$$

where:
ω=the radian frequency which equals 2π times the cyclic frequency, f; and
A=the zero-to-peak amplitude.

The longitudinal excursion is defined as the peak-to-peak (p-t-p) amplitude, which is just twice the amplitude of the sine wave or 2A.

Solid core ultrasonic surgical instruments may be divided into two types, single element end-effector devices and multiple-element end-effector. Single element end-effector devices include instruments such as scalpels, and ball coagulators, see, for example, U.S. Pat. No. 5,263,957. While such instruments as disclosed in U.S. Pat. No. 5,263,957 have been found eminently satisfactory, there are limitations with respect to their use, as well as the use of other ultrasonic surgical instruments. For example, single-element end-effector instruments have limited ability to apply blade-to-tissue pressure when the tissue is soft and loosely supported. Substantial pressure is necessary to effectively couple ultrasonic energy to the tissue. This inability to grasp the tissue results in a further inability to fully coapt tissue surfaces while applying ultrasonic energy, leading to less-than-desired hemostasis and tissue joining.

The use of multiple-element end-effectors such as clamping coagulators include a mechanism to press tissue against an ultrasonic blade, that can overcome these deficiencies. A clamp mechanism disclosed as useful in an ultrasonic surgical device has been described in U.S. Pat. Nos. 3,636,943 and 3,862,630 to Balamuth. Generally, however, the Balamuth device, as disclosed in those patents, does not coagulate and cut sufficiently fast, and lacks versatility in that it cannot be used to cut/coagulate without the clamp because access to the blade is blocked by the clamp.

Ultrasonic clamp coagulators such as, for example, those disclosed in U.S. Pat. Nos. 5,322,055 and 5,893,835 provide an improved ultrasonic surgical instrument for cutting/coagulating tissue, particularly loose and unsupported tissue, wherein the ultrasonic blade is employed in conjunction with a clamp for applying a compressive or biasing force to the tissue, whereby faster coagulation and cutting of the tissue, with less attenuation of blade motion, are achieved.

Improvements in technology of curved ultrasonic instruments such as described in U.S. patent application Ser. No. 09/106,686 previously incorporated herein by reference, have created needs for improvements in other aspects of curved clamp coagulators. For example, U.S. Pat. No. 5,873,873 describes an ultrasonic clamp coagulating instrument having an end-effector including a clamp arm comprising a tissue pad. In the configuration shown in U.S. Pat. No. 5,873,873 the clamp arm and tissue pad are straight.

The shape of an ultrasonic surgical blade or end-effector used in a clamp coagulator device defines at least four important aspects of the instrument. These are: (1) the visibility of the end-effector and its relative position in the surgical field, (2) the ability of the end-effector to access or approach targeted tissue, (3) the manner in which ultrasonic energy is coupled to tissue for cutting and coagulation, and (4) the manner in which tissue can be manipulated with the ultrasonically inactive end-effector. It would be advantageous to provide an improved ultrasonic clamp coagulator optimizing these four aspects of the instrument.

However, as features are added to ultrasonic surgical instrument blades, the altered shape and asymmetries cause the blade to become unbalanced, meaning that the blade has the tendency to vibrate in directions other than the longitudinal direction along the length of the instrument. U.S. patent application Ser. No. 09/106,686 previously incorporated herein by reference, addressed balancing blades proximal to functional asymmetries using balance asymmetries. While U.S. patent application Ser. No. 09/106,686 has proven eminently successful at balancing blades and waveguides proximal to the balance asymmetry, there are some applications where some balancing may be desirable within the functional portion of an asymmetric blade.

It would be desirable to provide a balanced ultrasonic surgical instrument blade within the functional area of the blade to optimize instrument performance. The blade described herein has been developed to address this desire.

SUMMARY OF THE INVENTION

Disclosed is an ultrasonic surgical instrument that combines end-effector geometry to best affect the multiple functions of a shears-type configuration. The shape of the blade is characterized by a radiused cut offset by some distance to form a curved geometry. The cut creates a curved surface with multiple asymmetries causing multiple imbalances within the blade. Imbalance due to the curve of the instrument is corrected by a non-functional asymmetry proximal to the functional asymmetry. Imbalance due to the asymmetric cross-section of the blade is corrected by the appropriate selection of the volume and location of material removed from a functional asymmetry. The shape of the blade in one embodiment of the present invention is characterized by two radiused cuts offset by some distance to form a curved and potentially tapered geometry. These two cuts create curved surfaces including a concave surface and a convex surface. The length of the radiused cuts affects, in part, the acoustic balancing of the transverse motion induced by the curved shape.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 14 is a side view of an inner knob of the clamp coagulator;

FIG. 15 is a front view of an inner knob of the clamp coagulator;

FIG. 16 is a bottom view of an inner knob of the clamp coagulator;

FIG. 27 is a top view of a tissue pad of the clamp coagulator;

FIG. 28 is a side view of a tissue pad of the clamp coagulator;

FIG. 29 is a front view of a tissue pad of the clamp coagulator;

DETAILED DESCRIPTION OF THE INVENTION

The present invention will be described in combination with ultrasonic instruments as described herein. Such description is exemplary only, and is not intended to limit the scope and applications of the invention. For example, the invention is useful in combination with a multitude of ultrasonic instruments including those described in, for example, U.S. Pat. Nos. 5,938,633; 5,935,144; 5,944,737; 5,322,055, 5,630,420; and 5,449,370.

Figure 1:
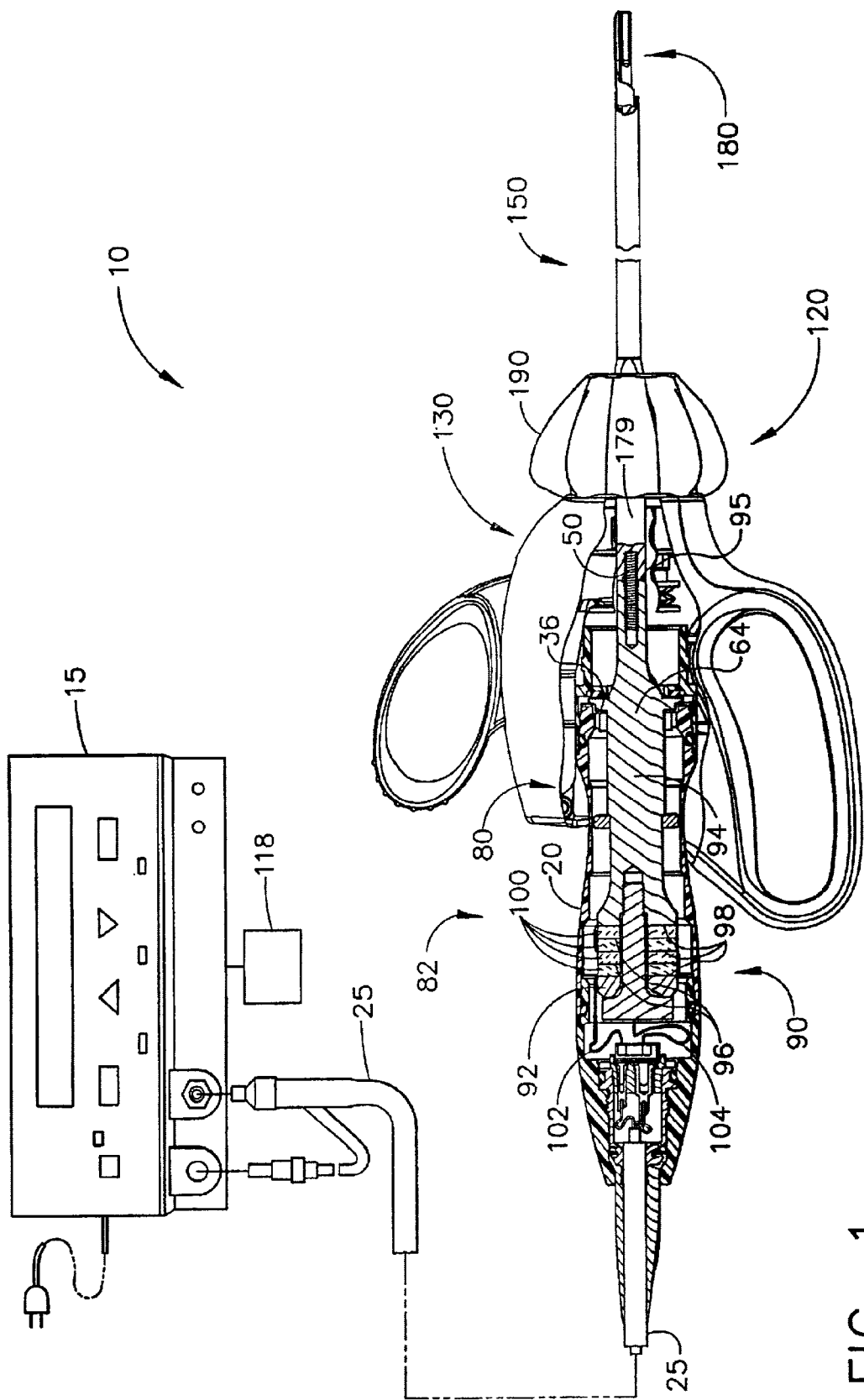
FIG. 1 illustrates an ultrasonic surgical system including an elevational view of an ultrasonic generator, a sectioned plan view of an ultrasonic transducer, and a partially sectioned plan view of a clamp coagulator in accordance with the present invention.

FIG. 1 illustrates ultrasonic system 10 comprising an ultrasonic signal generator 15 with ultrasonic transducer 82, hand piece housing 20, and clamp coagulator 120 in accordance with the present invention. Clamp coagulator 120 may be used for open or laparoscopic surgery. The ultrasonic transducer 82, which is known as a "Langevin stack", generally includes a transduction portion 90, a first resonator or end-bell 92, and a second resonator or fore-bell 94, and ancillary components. The ultrasonic transducer 82 is preferably an integral number of one-half system wavelengths ($n\lambda/2$) in length as will be described in more detail later. An acoustic assembly 80 includes the ultrasonic transducer 82, mount 36, velocity transformer 64 and surface 95.

The distal end of end-bell 92 is connected to the proximal end of transduction portion 90, and the proximal end of fore-bell 94 is connected to the distal end of transduction portion 90. Fore-bell 94 and end-bell 92 have a length determined by a number of variables, including the thickness of the transduction portion 90, the density and modulus of elasticity of the material used to manufacture end-bell 92 and fore-bell 94, and the resonant frequency of the ultrasonic transducer 82. The fore-bell 94 may be tapered inwardly from its proximal end to its distal end to amplify the ultrasonic vibration amplitude as velocity transformer 64, or alternately may have no amplification.

The piezoelectric elements 100 may be fabricated from any suitable material, such as, for example, lead zirconate-titanate, lead meta-niobate, lead titanate, or other piezoelectric crystal material. Each of the positive electrodes 96, negative electrodes 98, and piezoelectric elements 100 has a bore extending through the center. The positive and negative electrodes 96 and 98 are electrically coupled to wires 102 and 104, respectively. Wires 102 and 104 are encased within cable 25 and electrically connectable to ultrasonic signal generator 15 of ultrasonic system 10.

Ultrasonic transducer 82 of the acoustic assembly 80 converts the electrical signal from ultrasonic signal generator 15 into mechanical energy that results in primarily longitudinal vibratory motion of the ultrasonic transducer 82 and an end-effector 180 at ultrasonic frequencies. A suitable generator is available as model number GEN01, from Ethicon Endo-Surgery, Inc., Cincinnati, Ohio. When the acoustic assembly 80 is energized, a vibratory motion standing wave is generated through the acoustic assembly 80. The amplitude of the vibratory motion at any point along the acoustic assembly 80 depends on the location along the acoustic assembly 80 at which the vibratory motion is measured. A minimum or zero crossing in the vibratory motion standing wave is generally referred to as a node (i.e., where motion is usually minimal), and an absolute value maximum or peak in the standing wave is generally referred to as an anti-node. The distance between an anti-node and its nearest node is one-quarter wavelength ($\lambda/4$).

Wires 102 and 104 transmit the electrical signal from the ultrasonic signal generator 15 to positive electrodes 96 and negative electrodes 98. The piezoelectric elements 100 are energized by an electrical signal supplied from the ultrasonic signal generator 15 in response to a foot switch 118 to produce an acoustic standing wave in the acoustic assembly 80. The electrical signal causes disturbances in the piezoelectric elements 100 in the form of repeated small displacements resulting in large compression forces within the material. The repeated small displacements cause the piezoelectric elements 100 to expand and contract in a continuous manner along the axis of the voltage gradient, producing longitudinal waves of ultrasonic energy. The ultrasonic energy is transmitted through the acoustic assembly 80 to the end-effector 180.

In order for the acoustic assembly 80 to deliver energy to end-effector 180, all components of acoustic assembly 80 must be acoustically coupled to the ultrasonically active portions of clamp coagulator 120. The distal end of the ultrasonic transducer 82 may be acoustically coupled at surface 95 to the proximal end of an ultrasonic waveguide 179 by a threaded connection such as stud 50.

The components of the acoustic assembly 80 are preferably acoustically tuned such that the length of any assembly is an integral number of one-half wavelengths ($n\lambda/2$), where the wavelength $\lambda$ is the wavelength of a pre-selected or operating longitudinal vibration drive frequency $f_d$ of the acoustic assembly 80, and where n is any positive integer. It is also contemplated that the acoustic assembly 80 may incorporate any suitable arrangement of acoustic elements.

Figure 2A:
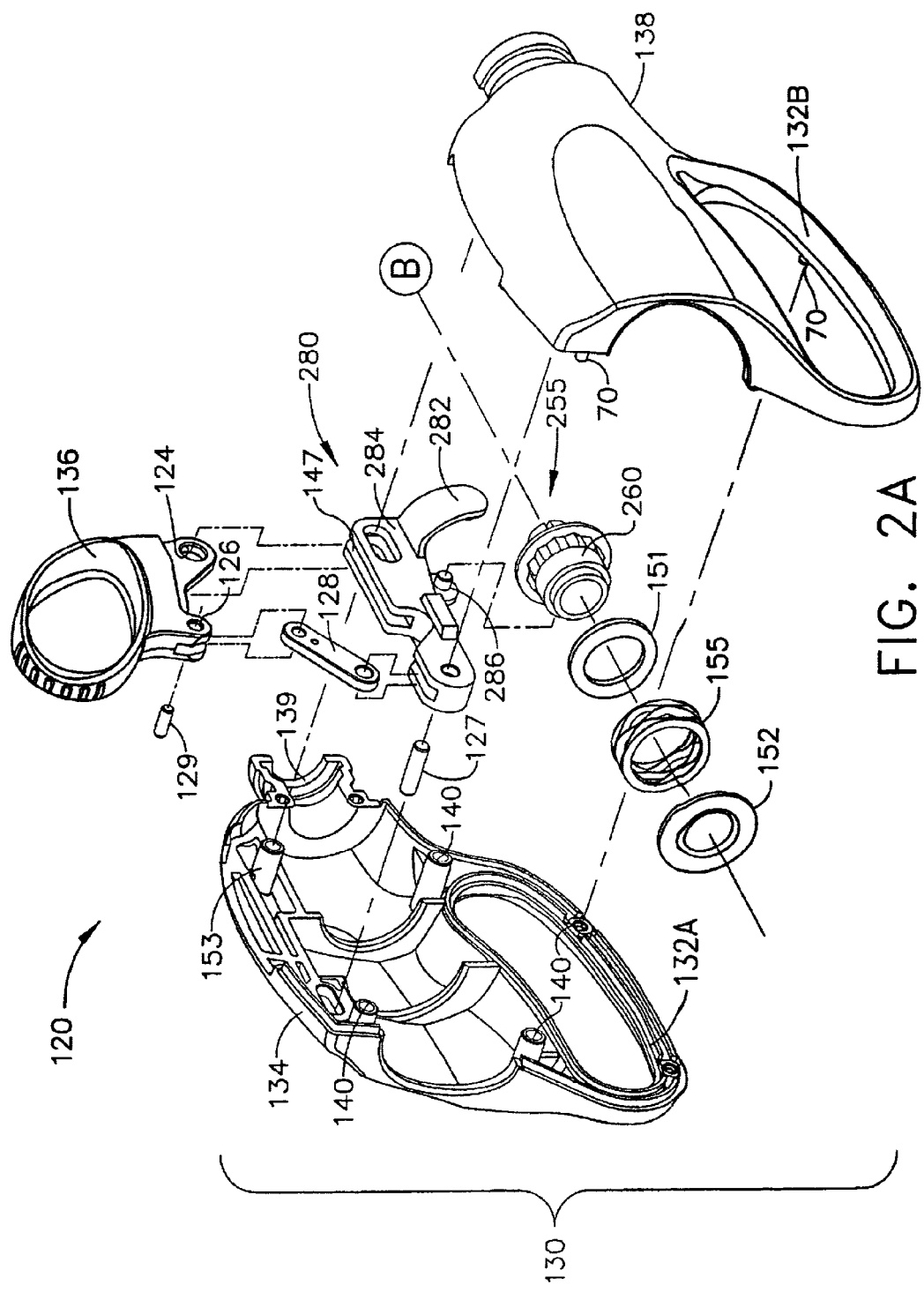
FIG. 2A is an exploded perspective view of a portion of a clamp coagulator in accordance with the present invention.
Figure 2B:
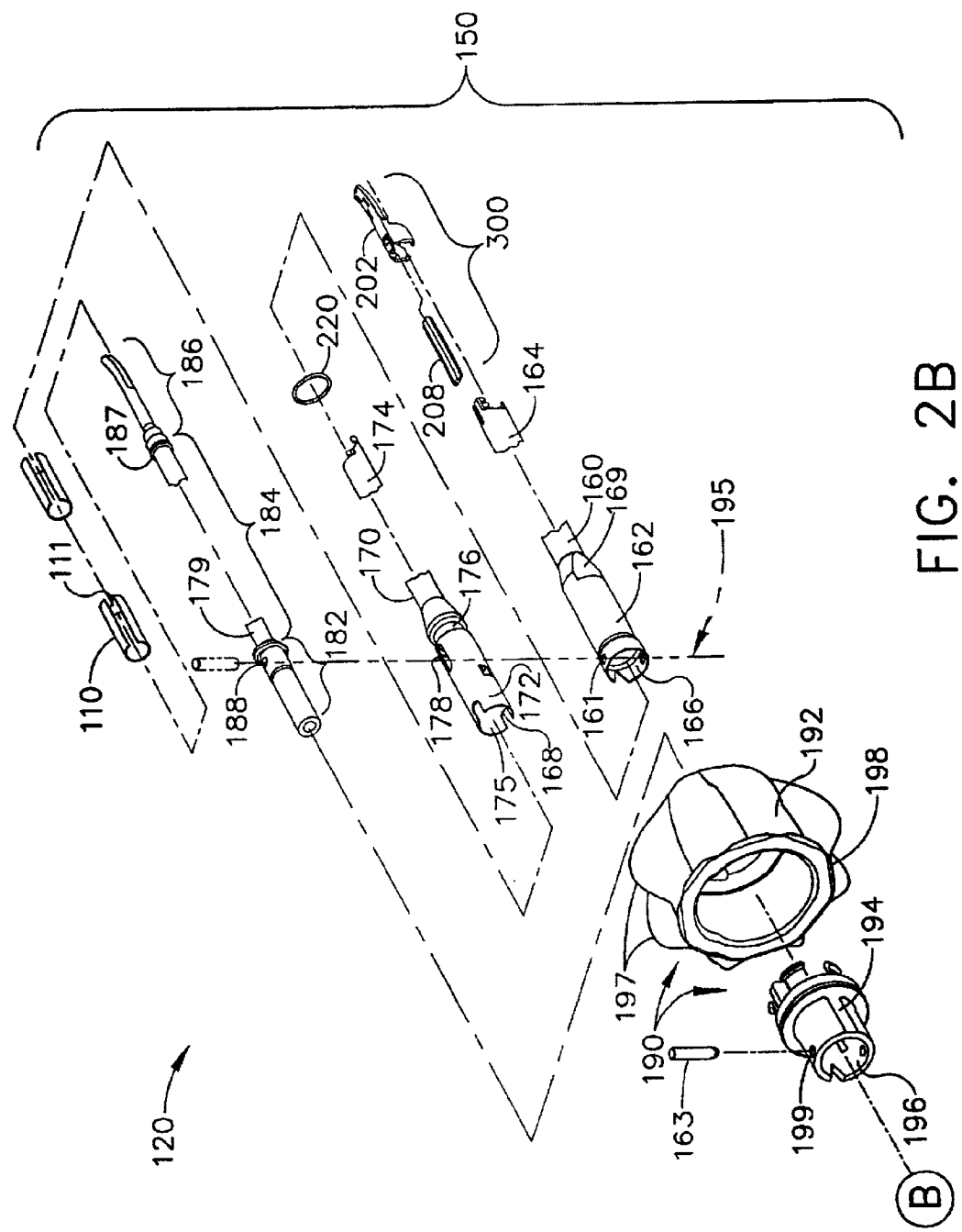
FIG. 2B is an exploded perspective view of a portion of a clamp coagulator in accordance with the present invention.

Referring now to FIGS. 2A and 2B, a clamp coagulator 120 of the surgical system 10 in accordance with the present invention is illustrated. The clamp coagulator 120 is preferably attached to and removed from the acoustic assembly 80 as a unit. The proximal end of the clamp coagulator 120 preferably acoustically couples to the distal surface 95 of the acoustic assembly 80 as shown in FIG. 1. It will be recognized that the clamp coagulator 120 may be coupled to the acoustic assembly 80 by any suitable means.

The clamp coagulator 120 preferably includes an instrument housing 130, and an elongated member 150. The elongated member 150 can be selectively rotated with respect to the instrument housing 130 as further described below. The instrument housing 130 includes a pivoting handle portion 136, and a fixed handle 132A and 132B, coupled to a left shroud 134 and a right shroud 138 respectively.

The right shroud 138 is adapted to snap fit on the left shroud 134. The right shroud 138 is preferably coupled to the left shroud 134 by a plurality of inwardly facing prongs 70 formed on the right shroud 138. The plurality of prongs 70 are arranged for engagement in corresponding holes or apertures 140, which are formed in the left shroud 134. When the left shroud 134 is attached to the right shroud 138, a cavity is formed therebetween to accommodate various components, such as an indexing mechanism 255 as further described below.

The left shroud 134, and the right shroud 138 of the clamp coagulator 120 are preferably fabricated from polycarbonate. It is contemplated that these components may be made from any suitable material without departing from the spirit and scope of the invention.

Indexing mechanism 255 is disposed in the cavity of the instrument housing 130. The indexing mechanism 255 is preferably coupled or attached on inner tube 170 to translate movement of the handle portion 136 to linear motion of the inner tube 170 to open and close the clamp arm assembly 300. When the pivoting handle portion 136 is moved toward the fixed handle portion 130, the indexing mechanism 255 slides the inner tube 170 rearwardly to pivot the clamp arm assembly 300 into a closed position. The movement of the pivoting handle portion 136 in the opposite direction slides the indexing mechanism 255 to displace the inner tube 170 in the opposite direction, i.e., forwardly, and hence pivot the clamp arm assembly 300 into its open position.

The indexing mechanism 255 also provides a ratcheting mechanism to allow the elongated member 150 to rotate about its longitudinal axis relative to instrument housing 130. The rotation of the elongated member 150 enables the clamp arm assembly 300 to be turned to a selected or desired angular position. The indexing mechanism 255 preferably includes a tubular collar 260 and yoke 280.

The tubular collar 260 of the indexing mechanism 255 is preferably snapped onto the proximal end of the inner tube 170 and keyed into opposing openings 168. The tubular collar 260 is preferably fabricated from polyetherimide. It is contemplated that the tubular collar 260 may be constructed from any suitable material.

Figure 11:
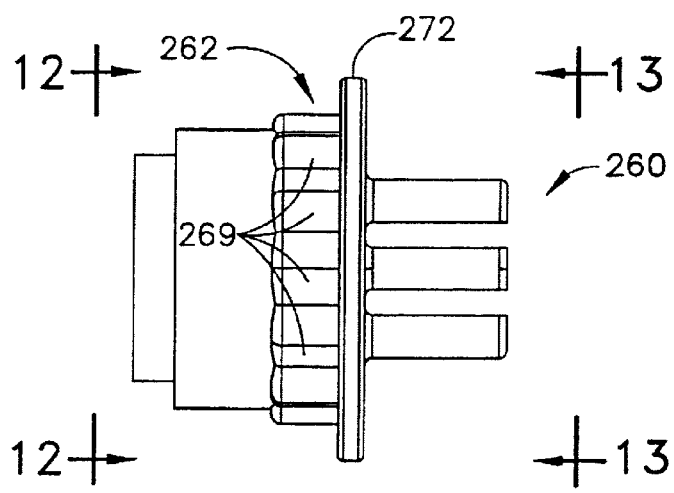
FIG. 11 is a side view of a tubular collar of the clamp coagulator.
Figures 12, 13:
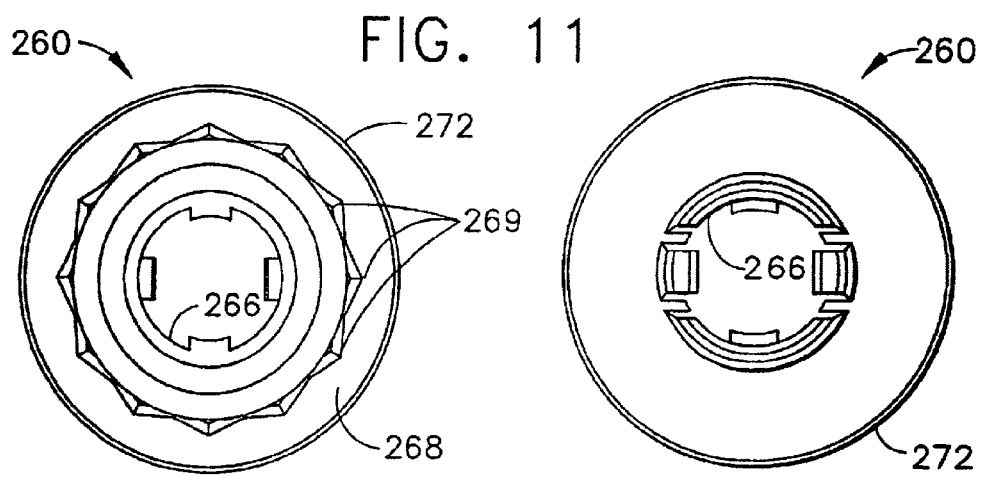
FIG. 12 is a rear view of a tubular collar of the clamp coagulator.
FIG. 13 is a front view of a tubular collar of the clamp coagulator.

Tubular collar 260 is shown in greater detail in FIGS. 11 through 13. The tubular collar 260 preferably includes an enlarged section 262, and a bore 266 extending therethrough. The enlarged section 262 preferably includes a ring 272 formed around the periphery of the tubular collar 260 to form groove 268. The groove 268 has a plurality of detents or teeth 269 for retaining the elongated member 150 in different rotational positions as the elongated member 150 is rotated about its longitudinal axis. Preferably, the groove 268 has twelve ratchet teeth to allow the elongated portion to be rotated in twelve equal angular increments of approximately 30 degrees. It is contemplated that the tubular collar 260 may have any number of teeth-like members. It will be recognized that the teeth-like members may be disposed on any suitable part of the tubular collar 260 without departing from the scope and spirit of the present invention.

Referring back now to FIGS. 2A through 4, the pivoting handle portion 136 includes a thumb loop 142, a first hole 124, and a second hole 126. A pivot pin 153 is disposed through first hole 124 of handle portion 136 to allow pivoting as shown by arrow 121 in FIG. 3. As thumb loop 142 of pivoting handle portion 136 is moved in the direction of arrow 121, away from instrument housing 130, a link 128 applies a forward force to yoke 280, causing yoke 280 to move forward. Link 128 is connected to pivoting handle portion 136 by a pin 129, and link 128 is connected to base 284 by a pin 127.

Referring back now to FIG. 2A, yoke 280 generally includes a holding or supporting member 282 and a base 284. The supporting member 282 is preferably semi-circular and has a pair of opposing pawls 286 that extend inwardly to engage with the teeth 269 of the tubular collar 260. It is contemplated that the pawls 286 may be disposed on any suitable part of the yoke 280 for engagement with the teeth 269 of the tubular collar 260 without departing from the spirit and scope of the invention. It will also be recognized that the yoke 280 may have any number of ratchet arms.

Yoke 280 is shown in greater detail in FIGS. 19 through 22. The pivoting handle portion 136 preferably is partially disposed in a slot 147 of the base 284 of the yoke 280. The base 284 also includes a base opening 287, an actuator travel stop 290, and a base pin-hole 288. The pivot pin 153 is disposed through the base opening 287. Yoke 280 pawls 286 transfer opening force to inner tube 170 through tubular collar 260, resulting in the opening of clamp arm assembly 300.

The yoke 280 of the clamp coagulator 120 is preferably fabricated from polycarbonate. The yoke 280 may also be made from a variety of materials including other plastics, such as ABS, NYLON, or polyetherimide. It is contemplated that the yoke 280 may be constructed from any suitable material without departing from the spirit and scope of the invention.

Figure 3:
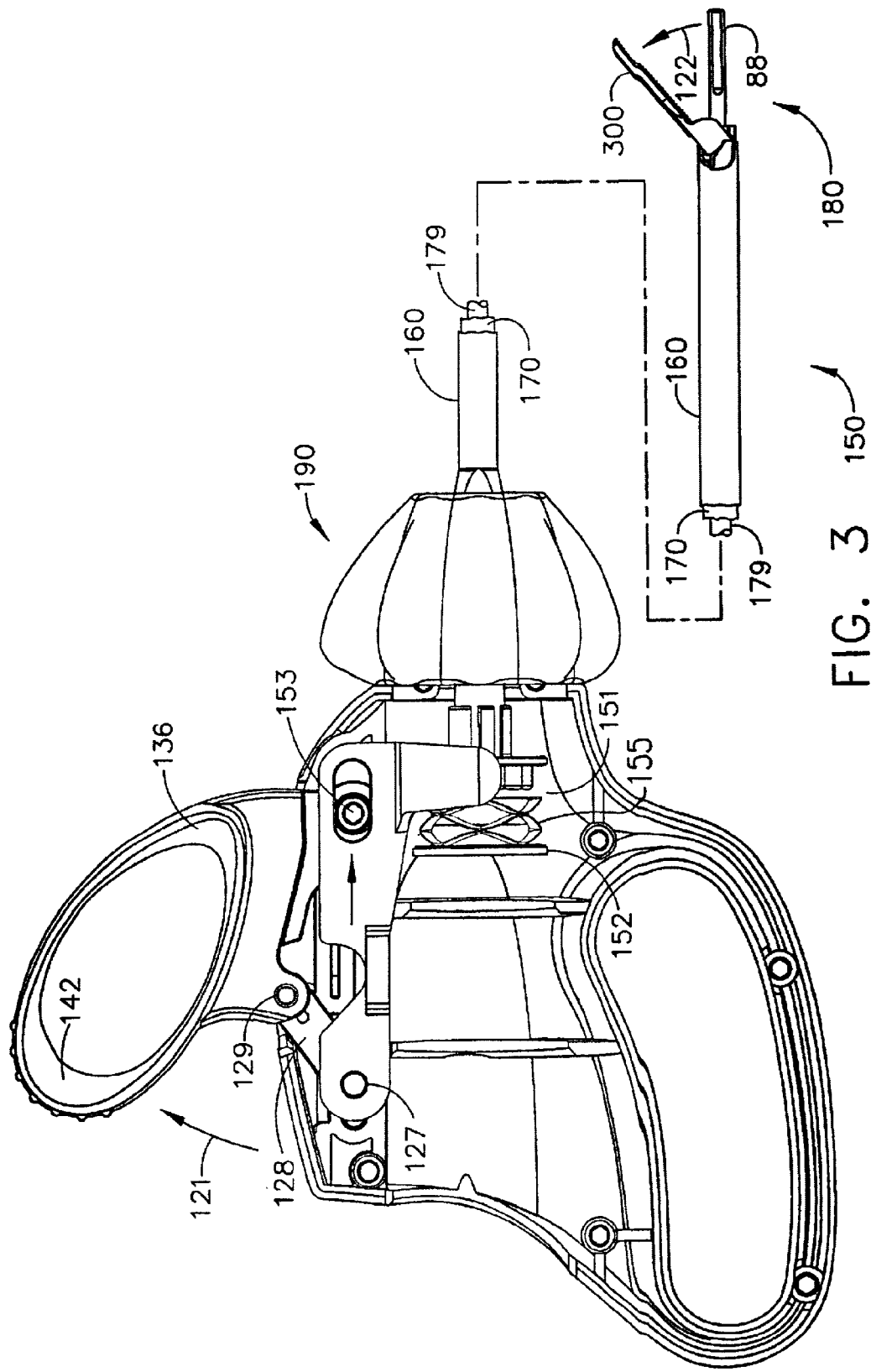
FIG. 3 is a partially sectioned plan view of a clamp coagulator in accordance with the present invention with the clamp arm assembly shown in an open position.
Figure 4:
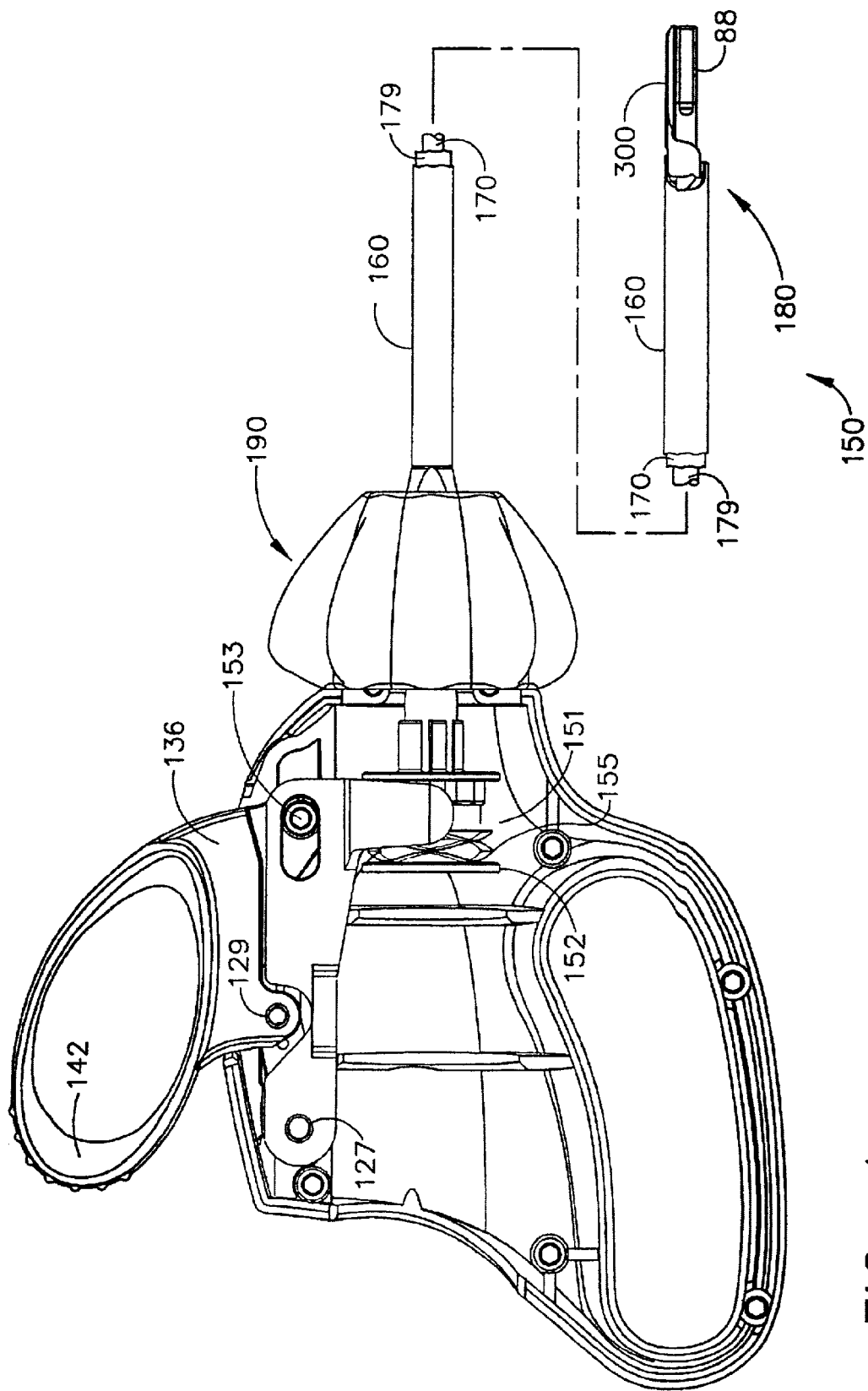
FIG. 4 is a partially sectioned plan view of a clamp coagulator in accordance with the present invention with the clamp arm assembly shown in a closed position.

As illustrated in FIGS. 3 and 4, yoke 280 also transfers a closing force to clamp arm assembly 300 as pivoting handle portion 136 is moved toward instrument housing 130. Actuator travel stop 290 contacts pivot pin 153 at the bottom of the stroke of pivoting handle portion 136, stopping any further movement, or overtravel, of pivoting handle portion 136. Pawls 286 of yoke 280 transfer force to tubular collar 260 through a washer 151, a force limiting spring 155, and collar cap 152. Collar cap 152 is rigidly attached to tubular collar 260 after washer 151 and force limiting spring 155 have been assembled onto tubular collar 260 proximal to enlarged section 262. Collar cap 152 is illustrated in greater detail in FIGS. 5 and 6. Force limiting spring 155 is illustrated in greater detail in FIGS. 7 and 8, and washer 151 is illustrated in greater detail in FIGS. 9 and 10. Thickness of washer 151 may be adjusted during design or manufacturing of clamp coagulator 120 to alter the pre-load of force limiting spring 155. Collar cap 152 is attached to tubular collar 260 by ultrasonic welding, but may alternately be press fit, snap fit or attached with an adhesive.

Referring to FIGS. 5 through 10, tubular collar 260, washer 151, force limiting spring 155, and collar cap 152 provide a force limiting feature to clamp arm assembly 300. As pivoting handle portion 136 is moved toward instrument housing 130, clamp arm assembly 300 is rotated toward ultrasonic blade 88. In order to provide both ultrasonic cutting, and hemostasis, it is desirable to limit the maximum force of clamp arm assembly 300 to 0.5 to 3.0 Lbs.

Figure 5:
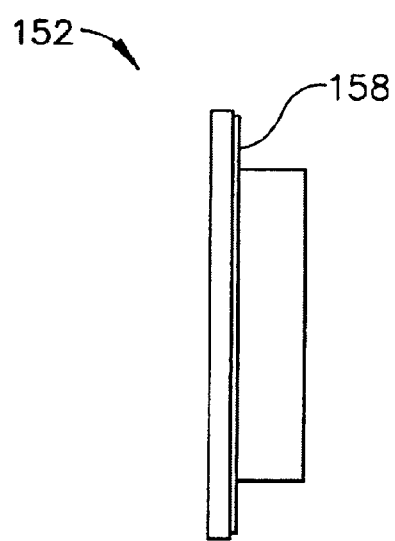
FIG. 5 is a side view of a collar cap of the clamp coagulator.
Figure 6:
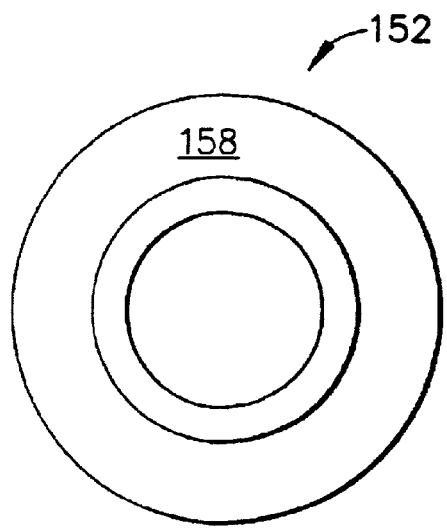
FIG. 6 is a front view of a collar cap of the clamp coagulator.
Figure 7:
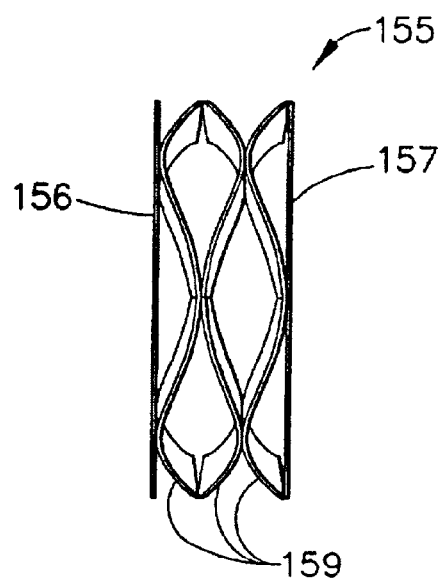
FIG. 7 is a side view of a force limiting spring of the clamp coagulator.
Figure 8:
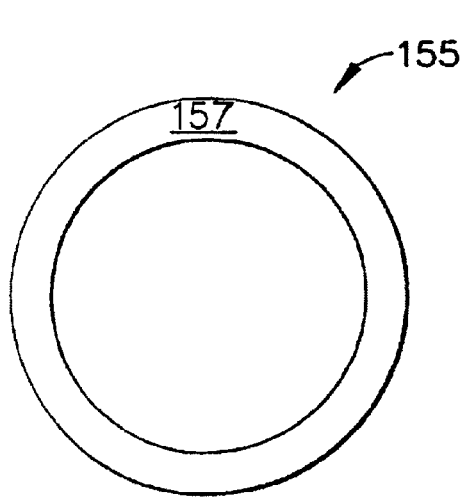
FIG. 8 is a front view of a force limiting spring of the clamp coagulator.
Figures 9, 10:
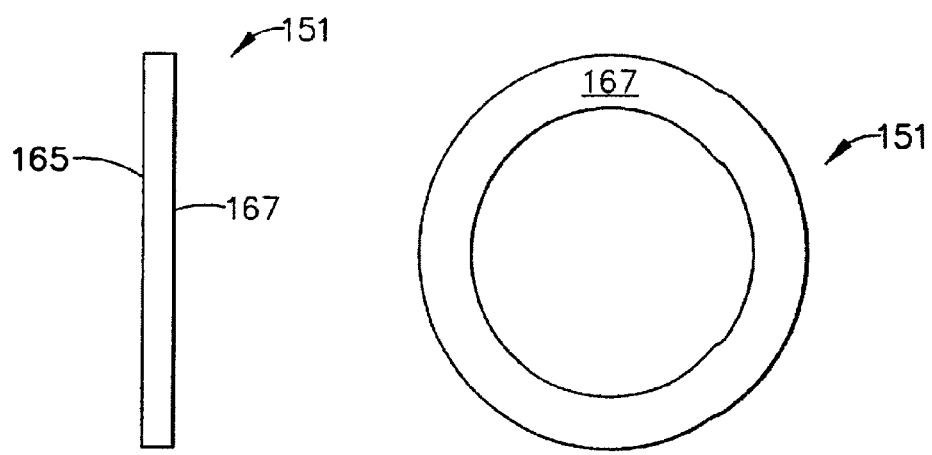
FIG. 9 is a side view of a washer of the clamp coagulator.
FIG. 10 is a front view of a washer of the clamp coagulator.

FIGS. 5 and 6 illustrate collar cap 152 including a spring surface 158. FIGS. 7 and 8 illustrate force limiting spring 155 including a cap surface 156, a washer surface 157, and a plurality of spring elements 159. Force limiting spring 155 is described in the art as a wave spring, due to the shape of spring elements 159. It is advantageous to use a wave spring for force limiting spring 155 because it provides a high spring rate in a small physical size well suited to an ultrasonic surgical instrument application where a central area is open for ultrasonic waveguide 179. Force limiting spring 155 is biased between spring surface 158 of collar cap 152 and spring face 165 of washer 151. Washer 151 includes a pawl face 167 (FIGS. 9 and 10) that contacts pawls 286 of yoke 280 after assembly of clamp coagulator 120 (see FIGS. 2 through 4).

Referring now to FIGS. 2A, 2B, and FIGS. 14 through 18, a rotational knob 190 is mounted on the elongated member 150 to turn the elongated member 150 so that the tubular collar 260 rotates with respect to the yoke 280. The rotational knob 190 may be fabricated from polycarbonate. The rotational knob 190 may also be made from a variety of materials including other plastics, such as a polyetherimide, nylon, or any other suitable material.

The rotational knob 190 preferably has an enlarged section or outer knob 192, an inner knob 194, and an axial bore 196 extending therethrough. Inner knob 194 includes keys 191 that attach cooperatively to keyways 189 of outer knob 192. The outer knob 192 includes alternating longitudinal ridges 197 and grooves 198 that facilitate the orientation of the rotational knob 190 and the elongated member 150 by a surgeon. The axial bore 196 of the rotational knob 190 is configured to snugly fit over the proximal end of the elongated member 150.

The inner knob 194 extends through an opening 139 in the distal end of the instrument housing 130. Inner knob 194 includes a channel 193 to rotatably attach inner knob 194 into opening 139. The inner knob 194 of the rotational knob 190 has a pair of opposing holes 199. The opposing holes 199 are aligned as part of a passageway 195 that extends through the elongated member 150, as will be described later.

A coupling member, such as, for example, pin 163, may be positioned through opposing holes 199 of the passageway 195. The pin 163 may be held in the passageway 195 of the elongated member 150 by any suitable means, such as, for example, trapped between ribs in housing 130, or a silicone or cyanoacrylate adhesive. The pin 163 allows rotational torque to be applied to the elongated member 150 from the rotational knob 190 in order to rotate the elongated member 150.

When the rotational knob 190 is rotated, the teeth 269 of the tubular collar 260 engage and ride up slightly on the corresponding pawls 286 of the yoke 280. As the pawls 286 ride up on the teeth 269, the supporting member 282 of the yoke 280 deflects outwardly to allow pawls 286 to slip or pass over the teeth 269 of the tubular collar 260.

In one embodiment, the teeth 269 of the tubular collar 260 are configured as ramps or wedges, and the pawls 286 of the yoke 280 are configured as posts. The teeth 269 of the tubular collar 260 and the pawls 286 of the yoke 280 may be reversed so that the teeth 269 of the tubular collar 260 are posts, and the pawls 286 of the yoke 280 are ramps or wedges. It is contemplated that the teeth 269 may be integrally formed or coupled directly to the periphery of the elongated member 150. It will also be recognized that the teeth 269 and the pawls 286 may be cooperating projections, wedges, cam surfaces, ratchet-like teeth, serrations, wedges, flanges, or the like which cooperate to allow the elongated member 150 to be indexed at selective angular positions, without departing from the spirit and scope of the invention.

As illustrated in FIG. 2B, the elongated member 150 of the clamp coagulator 120 extends from the instrument housing 130. As shown in FIGS. 2B through 4, the elongated member 150 preferably includes an outer member or outer tube 160, an inner member or inner tube 170, and a transmission component or ultrasonic waveguide 179.

The outer tube 160 of the elongated member 150 preferably includes a hub 162, a tubular member 164, and a longitudinal opening or aperture 166 extending therethrough. The outer tube 160 preferably has a substantially circular cross-section and may be fabricated from stainless steel. It will be recognized that the outer tube 160 may be constructed from any suitable material and may have any suitable cross-sectional shape.

The hub 162 of the outer tube 160 preferably has a larger diameter than the tubular member 164 does. The hub 162 has a pair of outer tube holes 161 to receive pin 163 to allow the hub 162 to be coupled to rotational knob 190. As a result, the outer tube 160 will rotate when the rotational knob 190 is turned or rotated.

The hub 162 of the outer tube 160 also includes wrench flats 169 on opposite sides of the hub 162. The wrench flats 169 are preferably formed near the distal end of the hub 162. The wrench flats 169 allow torque to be applied by a torque wrench to the hub 162 to tighten the ultrasonic waveguide 179 to the stud 50 of the acoustic assembly 80. For example, U.S. Pat. Nos. 5,059,210 and 5,057,119, which are hereby incorporated herein by reference, disclose torque wrenches for attaching and detaching a transmission component to a mounting device of a hand piece assembly.

Located at the distal end of the tubular member 164 of the outer tube 160 is an end-effector 180 for performing various tasks, such as, for example, grasping tissue, cutting tissue and the like. It is contemplated that the end-effector 180 may be formed in any suitable configuration.

Figure 23:
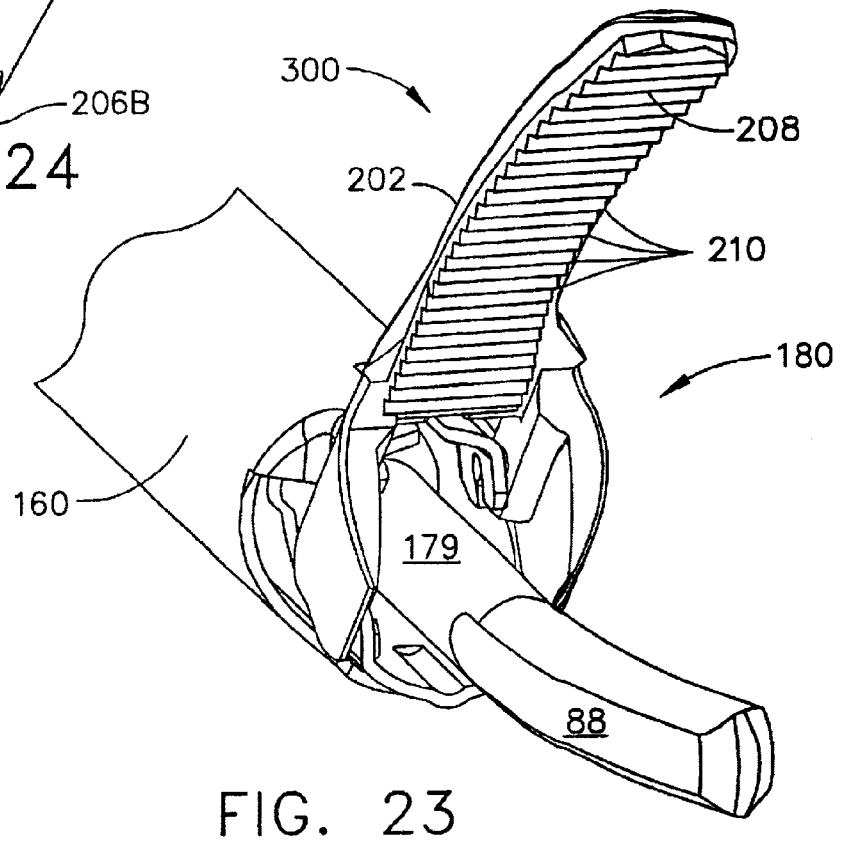
FIG. 23 is a perspective view of an end-effector of the clamp coagulator.
Figure 25:
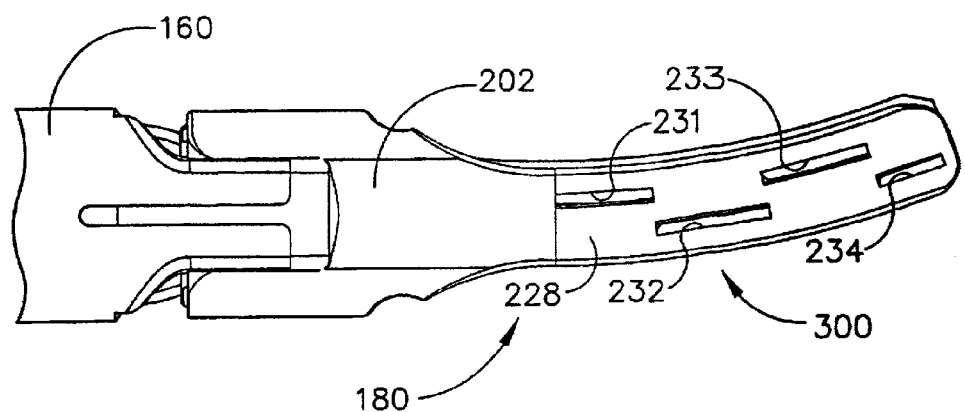
FIG. 25 is a top view of an end-effector of the clamp coagulator.
Figure 26:
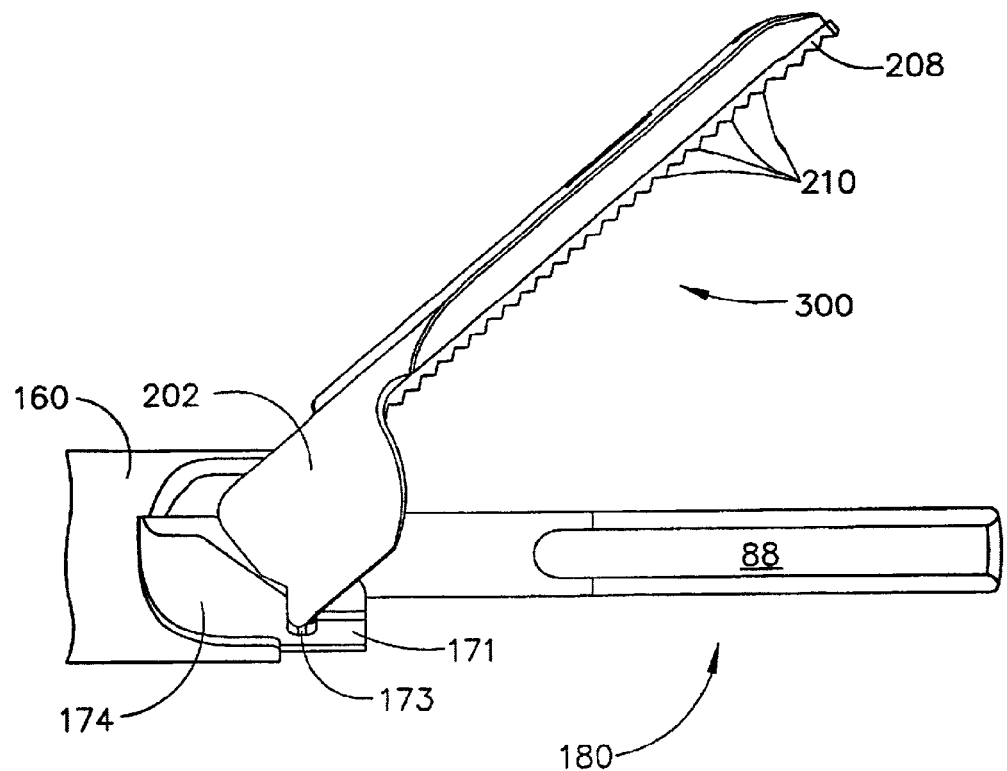
FIG. 26 is a side view of an end-effector of the clamp coagulator with the clamp arm open.

End-effector 180 and its components are shown in greater detail in FIGS. 23 through 33. The end-effector 180 generally includes a non-vibrating clamp arm assembly 300 to, for example, grip tissue or compress tissue against the ultrasonic blade 88. The end-effector 180 is illustrated in FIGS. 23 and 26 in a clamp open position, and clamp arm assembly 300 is preferably pivotally attached to the distal end of the outer tube 160.

Looking first to FIGS. 23 through 26, the clamp arm assembly 300 preferably includes a clamp arm 202, a jaw aperture 204, a first post 206A, a second post 206B, and a tissue pad 208. The clamp arm 202 is pivotally mounted about a pivot pin 207A and pivot pin 207B to rotate in the direction of arrow 122 in FIG. 3 when thumb loop 142 is moved in the direction indicated by arrow 121 in FIG. 3. By advancing the pivoting handle portion 136 toward the instrument housing 130, the clamp arm 202 is pivoted about the pivot pin 207A and pivot pin 207B into a closed position. Retracting the pivoting handle portion 136 away from the instrument housing 130 pivots the clamp arm 202 into an open position.

The clamp arm 202 has tissue pad 208 attached thereto for squeezing tissue between the ultrasonic blade 88 and clamp arm assembly 300. The tissue pad 208 is preferably formed of a polymeric or other compliant material and engages the ultrasonic blade 88 when the clamp arm 202 is in its closed position. Preferably, the tissue pad 208 is formed of a material having a low coefficient of friction but which has substantial rigidity to provide tissue-grasping capability, such as, for example, TEFLON, a trademark name of E. I. Du Pont de Nemours and Company for the polymer polytetraflouroethylene (PTFE). The tissue pad 208 may be mounted to the clamp arm 202 by an adhesive, or preferably by a mechanical fastening arrangement as will be described below.

As illustrated in FIGS. 23, 26 and 28, serrations 210 are formed in the clamping surfaces of the tissue pad 208 and extend perpendicular to the axis of the ultrasonic blade 88 to allow tissue to be grasped, manipulated, coagulated and cut without slipping between the clamp arm 202 and the ultrasonic blade 88.

Tissue pad 208 is illustrated in greater detail in FIGS. 27 through 29. Tissue pad 208 includes a T-shaped protrusion 212, a left protrusion surface 214, a right protrusion surface 216, a top surface 218, and a bottom surface 219. Bottom surface 219 includes the serrations 210 previously described. Tissue pad 208 also includes a beveled front end 209 to ease insertion during assembly as will be described below.

Referring now to FIG. 26, the distal end of the tubular member 174 of the inner tube 170 preferably includes a finger or flange 171 that extends therefrom. The flange 171 has an opening 173A and an opening 173B (not shown) to receive the first post 206A and second post 206B of the clamp arm 202. When the inner tube 170 of the elongated member 150 is moved axially, the flange 171 moves forwardly or rearwardly while engaging the first post 206A and second post 206B of the clamp arm assembly 300 to open and close the clamp arm 202.

Referring now to FIGS. 24, 25, and 31 through 33, the clamp arm 202 of end-effector 180 is shown in greater detail. Clamp arm 202 includes an arm top 228 and an arm bottom 230, as well as a straight portion 235 and a curved portion 236. Straight portion 235 includes a straight T-slot 226. Curved portion 236 includes a first top hole 231, a second top hole 232, a third top hole 233, a fourth top hole 234, a first bottom cut-out 241, a second bottom cut-out 242, a third bottom cut-out 243, a forth bottom cut-out 244, a first ledge 221, a second ledge 222, a third ledge 223, a fourth ledge 224, and a fifth ledge 225.

Top hole 231 extends from arm top 228 through clamp arm 202 to second ledge 222. Top hole 232 extends from arm top 228 through clamp arm 202 to third ledge 223. Top hole 233 extends from arm top 228 through clamp arm 202 to fourth ledge 224. Top hole 234 extends from arm top 228 through clamp arm 202 to fifth ledge 225. The arrangement of holes 231 through 234 and ledges 211 through 225 enables clamp arm 202 to include both the straight portion 235 and the curved portion 236, while being moldable from a process such as, for example, metal injection molding (MIM). Clamp arm 202 may be made out of stainless steel or other suitable metal utilizing the MIM process.

Figure 31:
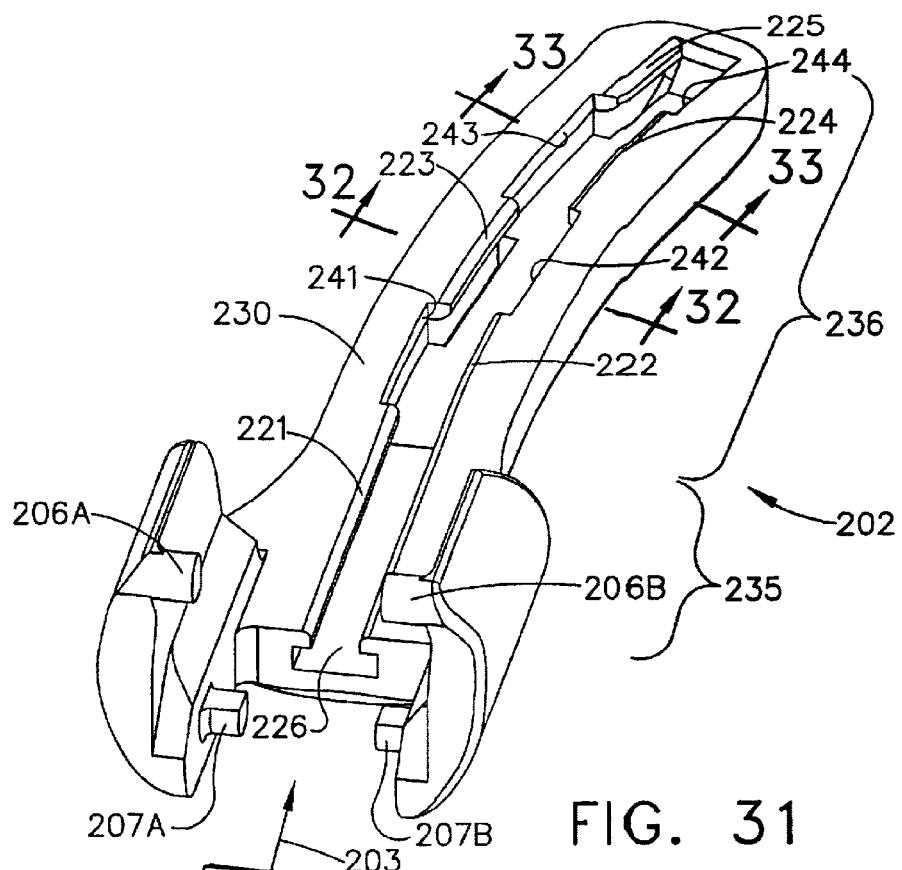
FIG. 31 is a bottom perspective view of a clamp arm of the clamp coagulator.
Figure 30:
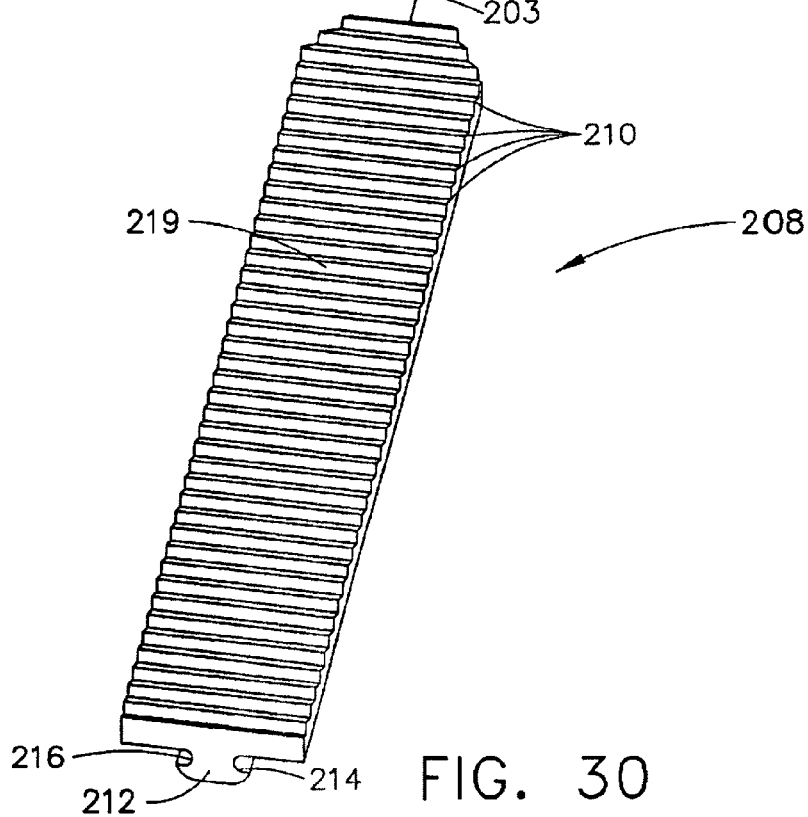
FIG. 30 is a perspective view of a tissue pad of the clamp coagulator.

Referring to FIGS. 30 and 31, tissue pad 208 T-shaped protrusion 212 is insertable into clamp arm 202 straight T-slot 226. Clamp arm 202 is designed such that tissue pad 208 may be manufactured as a straight component by, for example, injection molding, machining, or extrusion. As clamp arm 202 is inserted into straight T-slot 226 and moved progressively through curved portion 236, beveled front edge 209 facilitates bending of tissue pad 208 to conform to the curvature of clamp arm 202. The arrangement of holes 231 through 234 and ledges 211 through 225 enables clamp arm 202 to bend and hold tissue pad 208.

Figure 32:
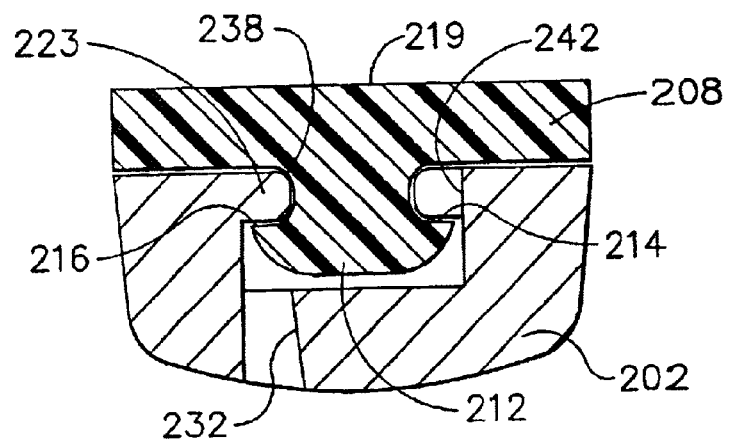
FIG. 32 is a first cross-sectional view of the clamp arm illustrated in FIG. 31.
Figure 33:
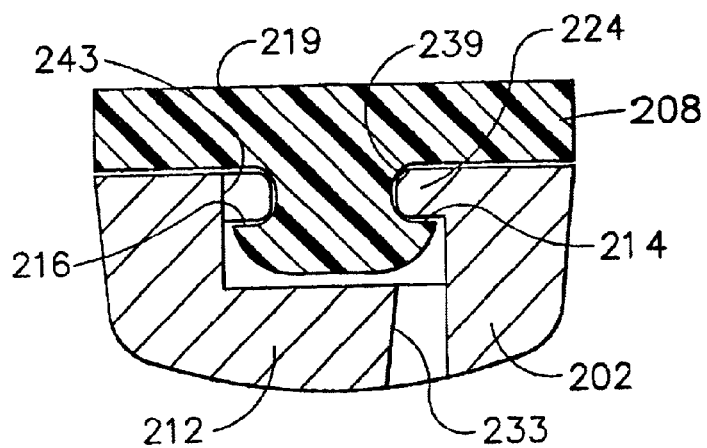
FIG. 33 is a second cross-sectional view of the clamp arm illustrated in FIG. 31.

FIGS. 32 and 33 illustrate how clamp arm 202 holds tissue pad 208 in place while maintaining a bend in tissue pad 208 that conforms to curved portion 236 of clamp arm 202. As illustrated in FIG. 32, third ledge 223 contacts right protrusion surface 216 providing a contact edge 238, while left protrusion surface 214 is unsupported at this position. At a distal location, illustrated in FIG. 33, fourth ledge 224 contacts left protrusion surface 214 providing a contact edge 239, while right protrusion surface 216 is unsupported at this location.

Referring back now to FIG. 2 again, the inner tube 170 of the elongated member 150 fits snugly within the opening 166 of the outer tube 160. The inner tube 170 preferably includes an inner hub 172, a tubular member 174, a circumferential groove 176, a pair of opposing openings 178, a pair of opposing openings 178, and a longitudinal opening or aperture 175 extending therethrough. The inner tube 170 preferably has a substantially circular cross-section, and may be fabricated from stainless steel. It will be recognized that the inner tube 170 may be constructed from any suitable material and may be any suitable shape.

The inner hub 172 of the inner tube 170 preferably has a larger diameter than the tubular member 174 does. The pair of opposing openings 178 of the inner hub 172 allow the inner hub 172 to receive the pin 163 to allow the inner tube 170 and the ultrasonic waveguide 179 to transfer torque for attaching ultrasonic waveguide 179 to stud 50 as previously described. An O-ring 220 is preferably disposed in the circumferential groove 176 of the inner hub 172.

The ultrasonic waveguide 179 of the elongated member 150 extends through aperture 175 of the inner tube 170. The ultrasonic waveguide 179 is preferably substantially semi-flexible. It will be recognized that the ultrasonic waveguide 179 may be substantially rigid or may be a flexible wire. Ultrasonic vibrations are transmitted along the ultrasonic waveguide 179 in a longitudinal direction to vibrate the ultrasonic blade 88.

The ultrasonic waveguide 179 may, for example, have a length substantially equal to an integral number of one-half system wavelengths ($n\lambda/2$). The ultrasonic waveguide 179 may be preferably fabricated from a solid core shaft constructed out of material which propagates ultrasonic energy efficiently, such as titanium alloy (i.e., Ti-6Al-4V) or an aluminum alloy. It is contemplated that the ultrasonic waveguide 179 may be fabricated from any other suitable material. The ultrasonic waveguide 179 may also amplify the mechanical vibrations transmitted to the ultrasonic blade 88 as is well known in the art.

As illustrated in FIG. 2, the ultrasonic waveguide 179 may include one or more stabilizing silicone rings or damping sheaths 110 (one being shown) positioned at various locations around the periphery of the ultrasonic waveguide 179. The damping sheaths 110 dampen undesirable vibration and isolate the ultrasonic energy from the inner tube 170 assuring the flow of ultrasonic energy in a longitudinal direction to the distal end of the ultrasonic blade 88 with maximum efficiency. The damping sheaths 110 may be secured to the ultrasonic waveguide 179 by an interference fit such as, for example, a damping sheath described in U.S. patent application Ser. No. 08/808,652 hereby incorporated herein by reference.

Referring again to FIG. 2, the ultrasonic waveguide 179 generally has a first section 182, a second section 184, and a third section 186. The first section 182 of the ultrasonic waveguide 179 extends distally from the proximal end of the ultrasonic waveguide 179. The first section 182 has a substantially continuous cross-section dimension.

The first section 182 preferably has at least one radial waveguide hole 188 extending therethrough. The waveguide hole 188 extends substantially perpendicular to the axis of the ultrasonic waveguide 179. The waveguide hole 188 is preferably positioned at a node but may be positioned at any other suitable point along the ultrasonic waveguide 179. It will be recognized that the waveguide hole 188 may have any suitable depth and may be any suitable shape.

The waveguide hole 188 of the first section 182 is aligned with the opposing openings 178 of the hub 172 and outer tube holes 161 of hub 162 to receive the pin 163. The pin 163 allows rotational torque to be applied to the ultrasonic waveguide 179 from the rotational knob 190 in order to rotate the elongated member 150. Passageway 195 of elongated member 150 includes opposing openings 178, outer tube holes 161, waveguide hole 188, and opposing holes 199.

The second section 184 of the ultrasonic waveguide 179 extends distally from the first section 182. The second section 184 has a substantially continuous cross-section dimension. The diameter of the second section 184 is smaller than the diameter of the first section 182. As ultrasonic energy passes from the first section 182 of the ultrasonic waveguide 179 into the second section 184, the narrowing of the second section 184 will result in an increased amplitude of the ultrasonic energy passing therethrough.

The third section 186 extends distally from the distal end of the second section 184. The third section 186 has a substantially continuous cross-section dimension. The third section 186 may also include small diameter changes along its length. The third section preferably includes a seal 187 formed around the outer periphery of the third section 186. As ultrasonic energy passes from the second section 184 of the ultrasonic waveguide 179 into the third section 186, the narrowing of the third section 186 will result in an increased amplitude of the ultrasonic energy passing therethrough.

The third section 186 may have a plurality of grooves or notches (not shown) formed in its outer circumference. The grooves may be located at nodes of the ultrasonic waveguide 179 or any other suitable point along the ultrasonic waveguide 179 to act as alignment indicators for the installation of a damping sheath 110 during manufacturing.

Still referring to FIG. 2, damping sheath 110 of the surgical instrument 150 surrounds at least a portion of the ultrasonic waveguide 179. The damping sheath 110 may be positioned around the ultrasonic waveguide 179 to dampen or limit transverse side-to-side vibration of the ultrasonic waveguide 179 during operation. The damping sheath 110 preferably surrounds part of the second section 184 of the ultrasonic waveguide 179. It is contemplated that the damping sheath 110 may be positioned around any suitable portion of the ultrasonic waveguide 179. The damping sheath 110 preferably extends over at least one antinode of transverse vibration, and more preferably, a plurality of antinodes of transverse vibration. The damping sheath 110 preferably has a substantially circular cross-section. It will be recognized that the damping sheath 110 may have any suitable shape to fit over the ultrasonic waveguide 179 and may be any suitable length.

The damping sheath 110 is preferably in light contact with the ultrasonic waveguide 179 to absorb unwanted ultrasonic energy from the ultrasonic waveguide 179. The damping sheath 110 reduces the amplitude of non-axial vibrations of the ultrasonic waveguide 179, such as, unwanted transverse vibrations associated with the longitudinal frequency of 55,500 Hz as well as other higher and lower frequencies.

The damping sheath 110 is constructed of a polymeric material, preferably with a low coefficient of friction to minimize dissipation of energy from the axial motion or longitudinal vibration of the ultrasonic waveguide 179. The polymeric material is preferably floura-ethylene propene (FEP) which resists degradation when sterilized using gamma radiation. It will be recognized that the damping sheath 110 may be fabricated from any suitable material, such as, for example, PTFE.

The damping sheath 110 preferably has an opening extending therethrough, and a longitudinal slit 111. The slit 111 of the damping sheath 110 allows the damping sheath 110 to be assembled over the ultrasonic waveguide 179 from either end. It will be recognized that the damping sheath 110 may have any suitable configuration to allow the damping sheath 110 to fit over the ultrasonic waveguide 179. For example, the damping sheath 110 may be formed as a coil or spiral or may have patterns of longitudinal and/or circumferential slits or slots. It is also contemplated that the damping sheath 110 may be fabricated without a slit 111 and the ultrasonic waveguide 179 may be fabricated from two or more parts to fit within the damping sheath 110.

It will be recognized that the ultrasonic waveguide 179 may have any suitable cross-sectional dimension. For example, the ultrasonic waveguide 179 may have a substantially uniform cross-section or the ultrasonic waveguide 179 may be tapered at various sections or may be tapered along its entire length.

The ultrasonic waveguide 179 may also amplify the mechanical vibrations transmitted through the ultrasonic waveguide 179 to the ultrasonic blade 88 as is well known in the art. The ultrasonic waveguide 179 may further have features to control the gain of the longitudinal vibration along the ultrasonic waveguide 179 and features to tune the ultrasonic waveguide 179 to the resonant frequency of the system.

The proximal end of the third section 186 of ultrasonic waveguide 179 may be coupled to the distal end of the second section 184 by an internal threaded connection, preferably near an antinode. It is contemplated that the third section 186 may be attached to the second section 184 by any suitable means, such as a welded joint or the like. Third section 186 includes ultrasonic blade 88. Although the ultrasonic blade 88 may be detachable from the ultrasonic waveguide 179, the ultrasonic blade 88 and ultrasonic waveguide 179 are preferably formed as a single unit.

The ultrasonic blade 88 may have a length substantially equal to an integral multiple of one-half system wavelengths ($n\lambda/2$). The distal end of ultrasonic blade 88 may be disposed near an antinode in order to provide the maximum longitudinal excursion of the distal end. When the transducer assembly is energized, the distal end of the ultrasonic blade 88 is configured to move in the range of, for example, approximately 10 to 500 microns peak-to-peak, and preferably in the range of about 30 to 150 microns at a predetermined vibrational frequency.

The ultrasonic blade 88 is preferably made from a solid core shaft constructed of material which propagates ultrasonic energy, such as a titanium alloy (i.e., Ti-6Al-4V) or an aluminum alloy. It will be recognized that the ultrasonic blade 88 may be fabricated from any other suitable material. It is also contemplated that the ultrasonic blade 88 may have a surface treatment to improve the delivery of energy and desired tissue effect. For example, the ultrasonic blade 88 may be micro-finished, coated, plated, etched, grit-blasted, roughened or scored to enhance coagulation and cutting of tissue and/or reduce adherence of tissue and blood to the end-effector. Additionally, the ultrasonic blade 88 may be sharpened or shaped to enhance its characteristics. For example, the ultrasonic blade 88 may be blade shaped, hook shaped, or ball shaped.

Figure 34:
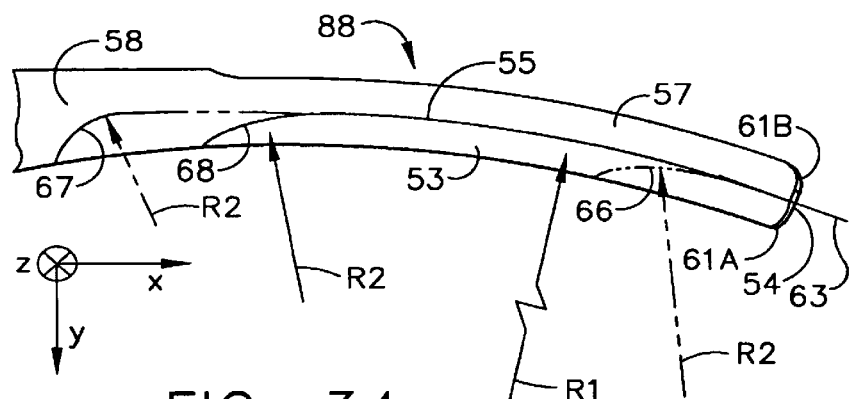
FIG. 34 is a bottom plan view of a blade of the clamp coagulator.
Figure 35:
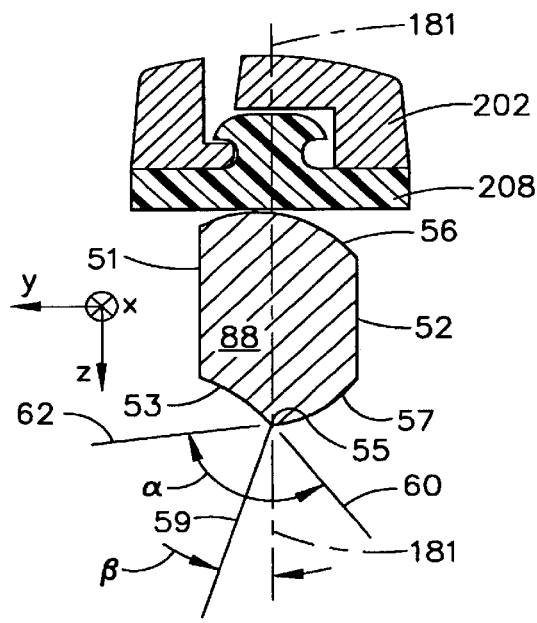
FIG. 35 is a cross-sectional view of a blade of the clamp coagulator.
Figure 36:
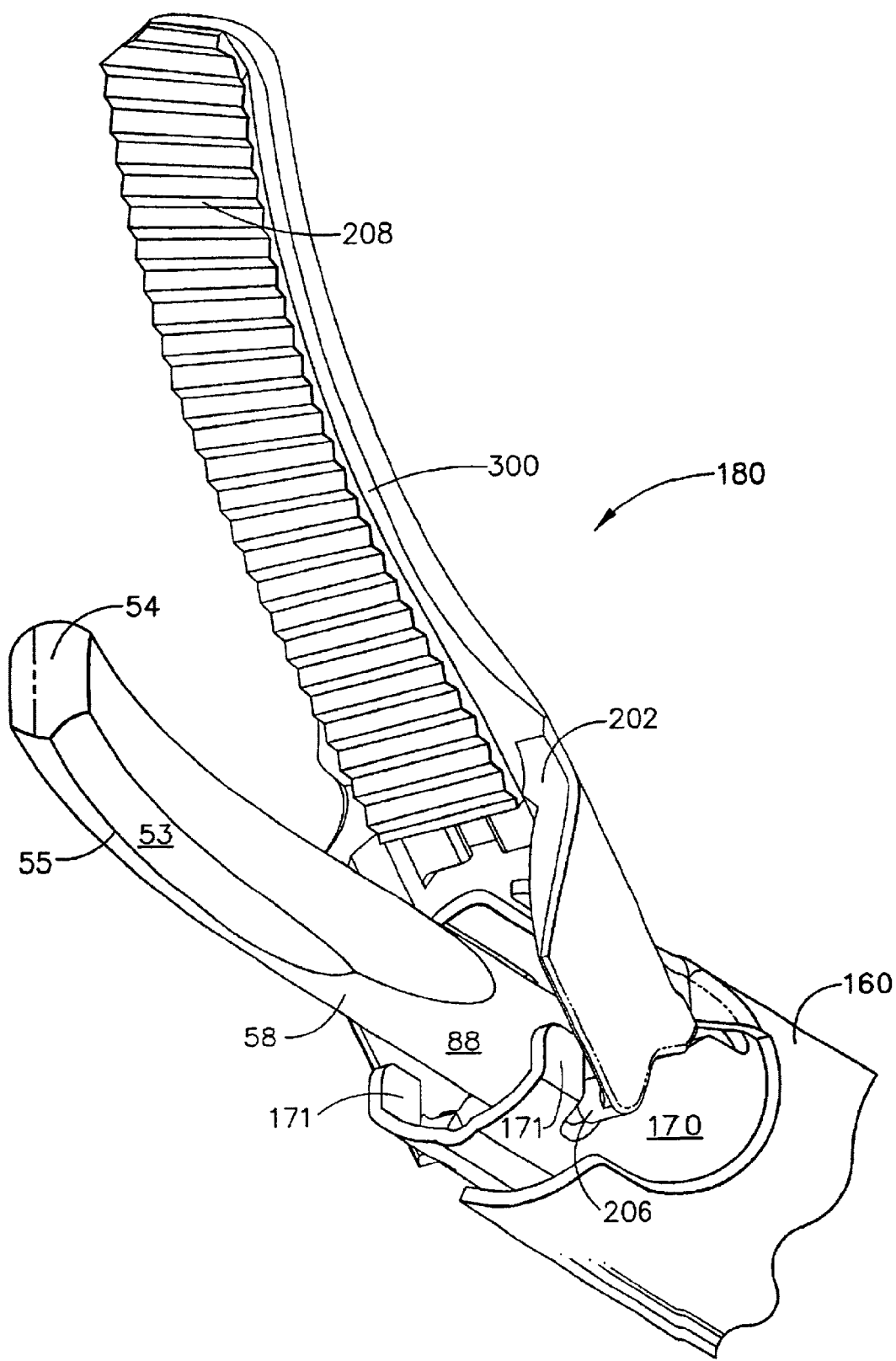
FIG. 36 is a perspective view of an end-effector of the clamp coagulator.

As illustrated in FIGS. 34, 35 and 36, the geometry of the ultrasonic blade 88 in accordance with the present invention delivers ultrasonic power more uniformly to clamped tissue than predicate devices. The end-effector 180 provides for improved visibility of the blade tip so that a surgeon can verify that the blade 88 extends across the structure being cut or coagulated. This is especially important in verifying margins for large blood vessels. The geometry also provides for improved tissue access by more closely replicating the curvature of biological structures. Blade 88 provides a multitude of edges and surfaces, designed to provide a multitude of tissue effects: clamped coagulation, clamped cutting, grasping, back-cutting, dissection, spot coagulation, tip penetration and tip scoring.

The distal most tip of blade 88 has a surface 54 perpendicular to tangent 63, a line tangent to the curvature at the distal tip. Two fillet-like features 61A and 61B are used to blend surfaces 51, 52 and 54, thus giving a blunt tip that can be utilized for spot coagulation. The top of the blade 88 is radiused and blunt, providing a broad edge, or surface 56, for clamping tissues between it and clamp arm assembly 300. Surface 56 is used for clamped cutting and coagulation as well as manipulating tissues while the blade is inactive.

The bottom surface has a spherical cut 53 that provides a narrow edge, or sharp edge 55, along the bottom of blade 88. The material cut is accomplished by, for example, sweeping a spherical end mill through an arc of radius R1 and then finishing the cut using a second, tighter radius R2 that blends the cut with a bottom surface 58 of the blade 88. Radius R1 is preferably within the range of 0.5 inches to 2 inches, more preferably within the range of 0.9 inches to 1.1 inches, and most preferably about 1.068 inches. Radius R2 is preferably within the range of 0.125 inches to 0.5 inches, and most preferably about 0.25 inches. The second radius R2 and the corresponding blend with the bottom surface 58 of blade 88 diminishes the stress concentrated at the end of the spherical cut relative to stopping the cut without this blend. The sharp edge 55 facilitates dissection and unclamped cutting (back-cutting) through less vascular tissues.

Spherical cut 53 on bottom surface 58 of blade 88 creates sharp edge 55 while removing a minimal amount of material from blade 88. Spherical cut 53 on the bottom of blade 88 creates a sharp edge 55 with an angle of α as described below. This angle α may be similar to predicate shears devices such as, for example, the LCS-K5 manufactured by Ethicon Endo-Surgery, Inc., Cincinnati, Ohio. However the blade 88 of the present invention cuts faster than predicate devices by virtue of the orientation of the angle α with respect to the typical application force. For the predicate shears devices, the edges are symmetric, spanning the application force equally. The edges for the present invention are asymmetric, with the asymmetry of the edges dictating how quickly tissue is separated or cut. The asymmetry is important in that it provides for an effectively sharper edge when ultrasonically activated, without removing a significant volume of material, while maintaining blunt geometry. This asymmetric angle as well as the curvature of the blade act to self tension tissue during back-cutting utilizing a slight hook-like or wedge-like action.

Sharp edge 55 of ultrasonic blade 88 is defined by the intersection of surface 53 and a second surface 57 left after bottom surface 58 has received spherical cut 53. Clamp arm assembly 300 is pivotally mounted on said distal end of outer tube 160 for pivotal movement with respect to ultrasonic blade 88, for clamping tissue between clamp arm assembly 300 and ultrasonic blade 88. Reciprocal movement of inner tube 170 pivots clamp arm assembly 300 through an arc of movement, defining a vertical plane 181. A tangent 60 of spherical cut 53 at sharp edge 55 defines an angle α with a tangent 62 of second surface 57, as illustrated in FIG. 35. The bisection 59 of angle α preferably does not lie in vertical plane 181, but is offset by an angle β. Preferably the tangent 60 of spherical cut 53 lies within about 5 to 50 degrees of vertical plane 181, and most preferably the tangent of spherical cut 53 lies about 38.8 degrees from vertical plane 181. Preferably angle α is within the range of about 90 to 150 degrees, and most preferably angle α is about 121.6 degrees.

Figure 35A:
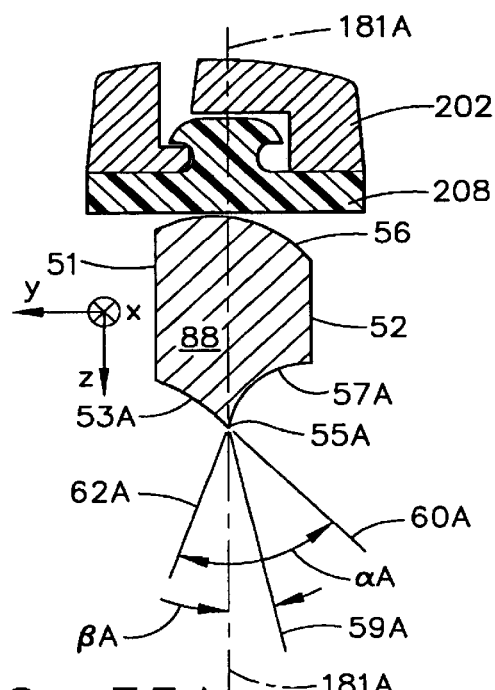
FIG. 35A is a cross-sectional view of an alternate embodiment of a blade of the clamp coagulator.

Looking to FIG. 35A, an alternate embodiment of the present invention is illustrated with an asymmetric narrow edge. A tangent 60A of a spherical cut 53A at a sharp edge 55A defines an angle αA with a tangent 62A of a second surface 57A, as illustrated in FIG. 35A. A bisection 59A of angle αA preferably does not lie in a vertical plane 181A, but is offset by an angle βA.

The curved shape of the design of ultrasonic blade 88 also results in a more uniformly distributed energy delivery to tissue as it is clamped against the blade 88. Uniform energy delivery is desired so that a consistent tissue effect (thermal and transection effect) along the length of end-effector 180 is achieved. The distal most 15 millimeters of blade 88 is the working portion, used to achieve a tissue effect. As will be further described below, the displacement vectors for locations along the curved shears blade 88 have directions that, by virtue of the improvements of the present invention over predicate instruments, lie largely in the x-y plane illustrated in FIGS. 34 and 35. The motion, therefore, of blade 88 lies within a plane (the x-y plane) that is perpendicular to the direction of the clamping force from clamp arm assembly 300.

Straight symmetric ultrasonic blades in general have tip excursions that lie along the longitudinal axis, designated the x-axis in FIGS. 34 and 35. Transverse motion is usually undesirable because it results in undesirable heat generation in inner tube 170. When a functional asymmetry is added to an ultrasonic blade, such as a curved end-effector as described in U.S. patent application Ser. No. 09/106,686 previously incorporated herein by reference, the functional asymmetry creates an imbalance in the ultrasonic waveguide. If the imbalance is not corrected, then undesirable heat, noise, and compromised tissue effect occur. Although U.S. patent application Ser. No. 09/106,686 teaches how to provide ultrasonic blades that are balanced proximal to the balance asymmetry, the distal portion of the end-effector has an excursion in at least two axes. If the end-effector has a single plane of functional asymmetry, such as a curved end-effector, but the blade is otherwise symmetric, then the excursion will lie in a plane at the distal most end.

It is often desirable to minimize any ultrasonic blade 88 excursion in the z-axis direction. Excursion of ultrasonic blade 88 in the z-axis direction causes system inefficiencies, resulting in undesirable heating, power loss, and possibly noise. Excursion of ultrasonic blade 88 in the z-axis direction at end-effector 180 causes the ultrasonic blade 88 to impact tissue lying between ultrasonic blade 88 and clamp arm assembly 300. It is desirable to limit ultrasonic blade 88 excursion to the x-y plane shown in FIGS. 34 and 35. This allows ultrasonic blade 88 to rub tissue lying between ultrasonic blade 88 and clamp arm assembly 300 without impact, which optimizes heating of the tissue, and thus provides optimal coagulation. Minimizing z-axis excursion both proximal to the end-effector 180, and in ultrasonic blade 88, may be accomplished by proper selection of a spherical cut 53.

However, an ultrasonic end-effector 180 with an ultrasonic blade 88 that has multiple functional asymmetries, such as ultrasonic blade 88 as illustrated in FIGS. 34 through 36, will naturally have a tendency to include tip excursion in all three axes, x, y, and z if not balanced properly. For example, ultrasonic blade 88 as illustrated in FIG. 34 is curved in the y direction at its distal end. This curvature, although balanced proximal to end-effector 180, will cause ultrasonic blade 88 to have excursions in both the x and y directions when activated. Adding spherical cut 53 subsequently adds another level of asymmetry to ultrasonic blade 88, causing tip excursion in all three axes if not corrected, and also causing z-axis imbalances in ultrasonic waveguide 179 which decreases efficiency.

It is possible to minimize z-axis tip excursion proximal to the functional asymmetry, and therefore maximize efficiency with improved tissue effect, by providing a functional asymmetry optimized to minimize z-axis excursion in ultrasonic waveguide 179. As illustrated in FIG. 34, spherical cut 53 may extend proximally into ultrasonic blade 88, from the most distal end, to any position. For example, FIG. 34 illustrates a first position 66, a second position 67, and a third position 68, for spherical cut 53 to extend into ultrasonic blade 88.

Table 1 below describes three possible lengths of spherical cuts 53 for ultrasonic blade 88 illustrated in FIG. 34 as first position 66, second position 67, and third position 68. The rows of Table 1 correspond to the length of cut into the ultrasonic blade 88, and the columns of Table 1 correspond to the balance condition and excursions along each axis for each cut length. It can be appreciated from Table 1 that providing spherical cut 53 to a length corresponding to first position 68 minimizes the z axis excursion proximal to the functional asymmetry. It is preferable to balance ultrasonic blade 88 below 15% z axis excursion proximal to the functional asymmetry and it is most preferable to balance ultrasonic blade 88 below 5% z axis excursion proximal to the functional asymmetry. Preferably clamp coagulator 120 is designed to be balanced when activated in air (loaded only by air), and then balance is verified under other load conditions.

In Table 1, a normalized excursion percentage (% z) in a clamping instrument at the end-effector 88 is calculated by taking the magnitude of the excursion in the direction normal to the clamp arm when the clamp arm is in its fully closed position, and dividing that magnitude by the magnitude of the maximum tip vibration excursion (also called the primary tip vibration excursion), and then multiplying the dividend by one hundred. Primary tip vibration excursion is the magnitude of the major axis of the ellipse or ellipsoid created by a point on the distal most end of ultrasonic blade 88 when the ultrasonic blade 88 is activated. The measurement of excursions is more fully explained in IEC international standard 61847, titled *Measurement and Declaration of the Basic Output Characteristics* of ultrasonic surgical systems, hereby incorporated herein by reference. A normalized excursion percentage (% x, % y, % z) in ultrasonic blade 88 or ultrasonic waveguide 179 is calculated by taking the magnitude of a secondary vibration excursion, and dividing that magnitude by the magnitude of the primary tip vibration excursion, and then multiplying the dividend by one hundred. Secondary tip vibration excursion is the magnitude of a minor axis, or other arbitrary axis, of the ellipse or ellipsoid created by a point on the distal most end of ultrasonic blade 88 when the ultrasonic blade 88 is activated.

TABLE 1

Three possible lengths to provide a range of balances for a 0.946 inch long blade with a radius of R1 manufactured from Ti6A14V with the blade including a functional asymmetry

| | % x at distal end of blade 88 | % y at distal end of blade 88 | % z at distal end of blade 88 | % z proximal to blade 88 |
|---|---|---|---|---|
| CutLength = 12.8 mm, Location at first position 68 | 71.83 | 69.47 | 4.15 | 0.40 |
| Cut Length = 14.8 mm, Location at second position 67 | 72.49 | 68.87 | 1.60 | 12.43 |
| Cut Length = 8.2 mm, Location at third position 66 | 74.54 | 66.03 | 9.21 | 8.25 |

Referring now to FIGS. 1–4, the procedure to attach and detach the clamp coagulator 120 from the acoustic assembly 80 will be described below. When the physician is ready to use the clamp coagulator 120, the physician simply attaches the clamp coagulator 120 onto the acoustic assembly 80. To attach the clamp coagulator 120 to acoustic assembly 80, the distal end of stud 50 is threadedly connected to the proximal end of the transmission component or ultrasonic waveguide 179. The clamp coagulator 120 is then manually rotated in a conventional screw-threading direction to interlock the threaded connection between the stud 50 and the ultrasonic waveguide 179.

Once the ultrasonic waveguide 179 is threaded onto the stud 50, a tool, such as, for example, a torque wrench, may be placed over the elongated member 150 of the clamp coagulator 120 to tighten the ultrasonic waveguide 179 to the stud 50. The tool may be configured to engage the wrench flats 169 of the hub 162 of the outer tube 160 in order to tighten the ultrasonic waveguide 179 onto the stud 50. As a result, the rotation of the hub 162 will rotate the elongated member 150 until the ultrasonic waveguide 179 is tightened against the stud 50 at a desired and predetermined torque. It is contemplated that the torque wrench may alternately be manufactured as part of the clamp coagulator 120, or as part of the hand piece housing 20, such as the torque wrench described in U.S. Pat. No. 5,776,155 hereby incorporated herein by reference.

Figure 17:
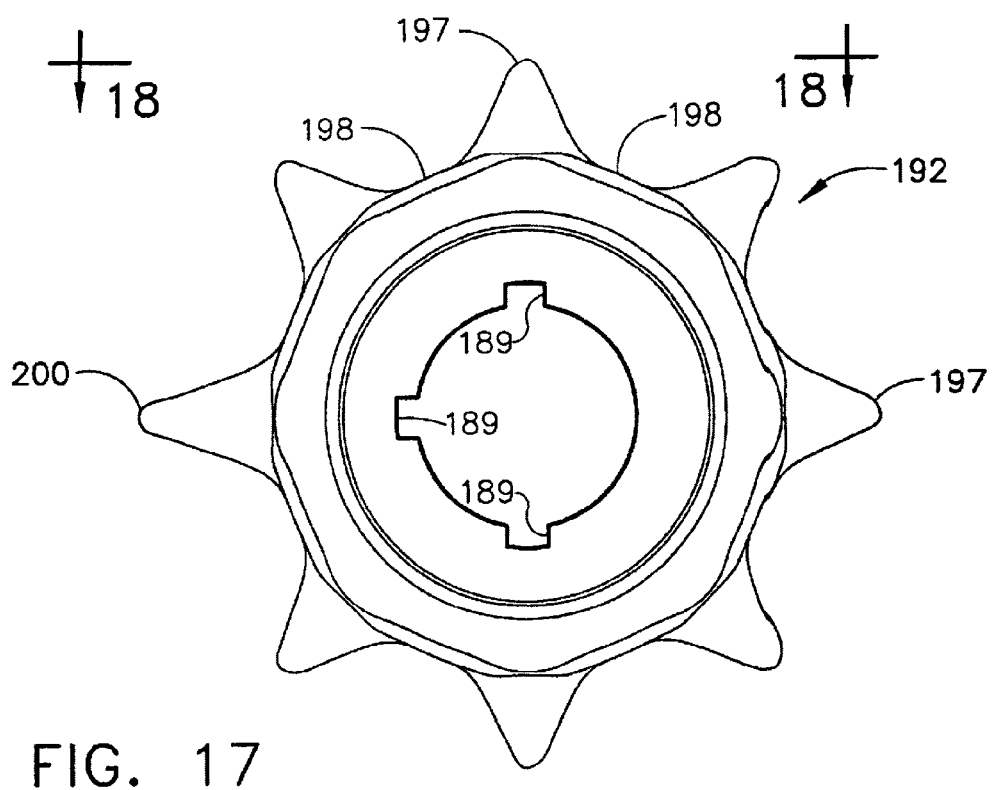
FIG. 17 is a rear view of an outer knob of the clamp coagulator.
Figure 18:
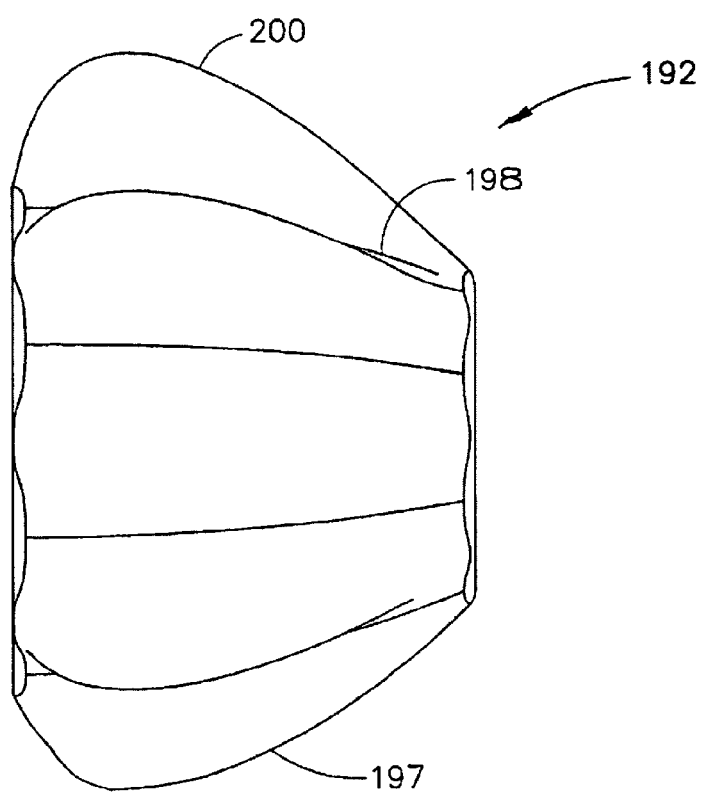
FIG. 18 is a top view of an outer knob of the clamp coagulator.
Figure 22:
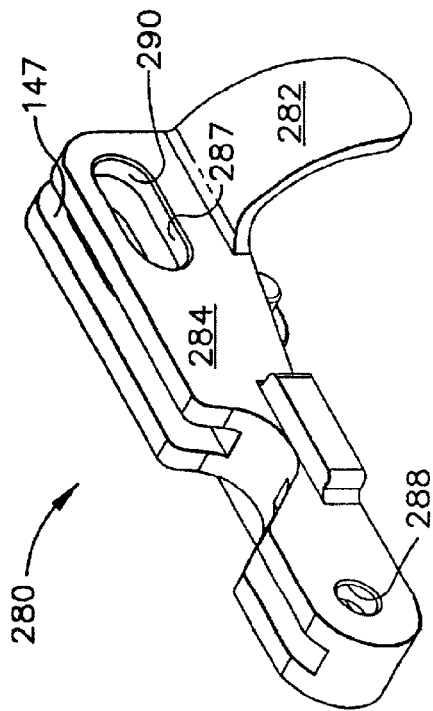
FIG. 22 is a perspective view of a yoke of the clamp coagulator.
Figure 21:
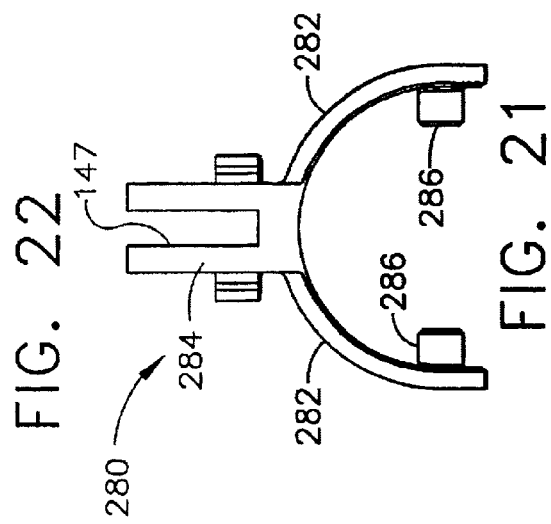
FIG. 21 is a front view of a yoke of the clamp coagulator.
Figure 19:
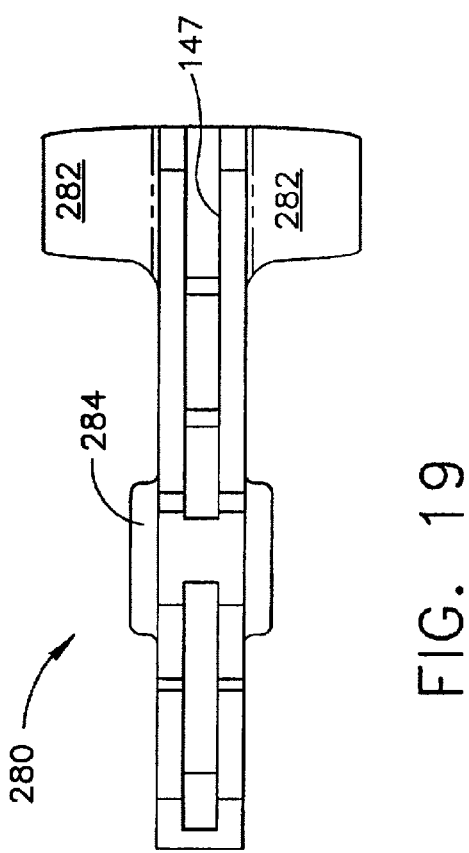
FIG. 19 is a top view of a yoke of the clamp coagulator.
Figure 20:
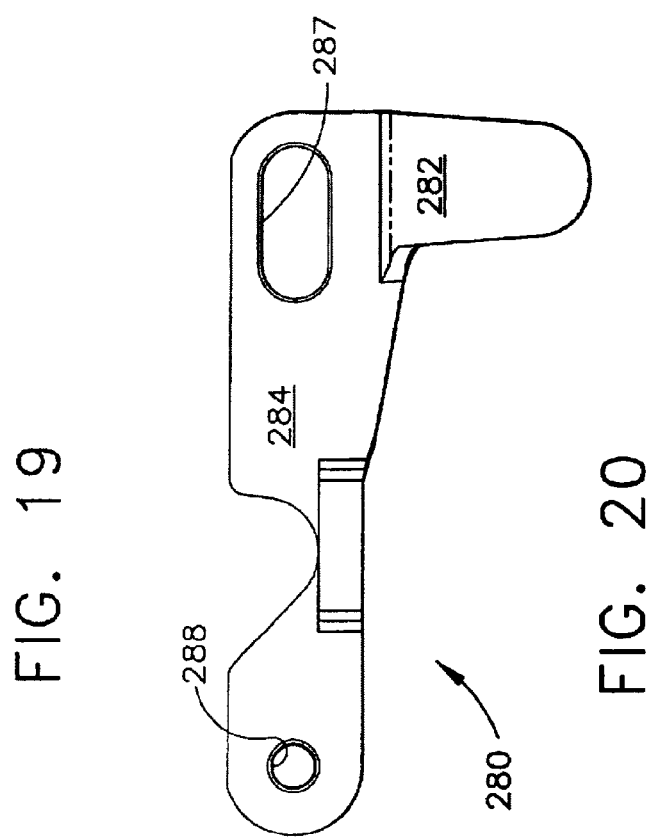
FIG. 20 is a side view of a yoke of the clamp coagulator.
Figure 24:
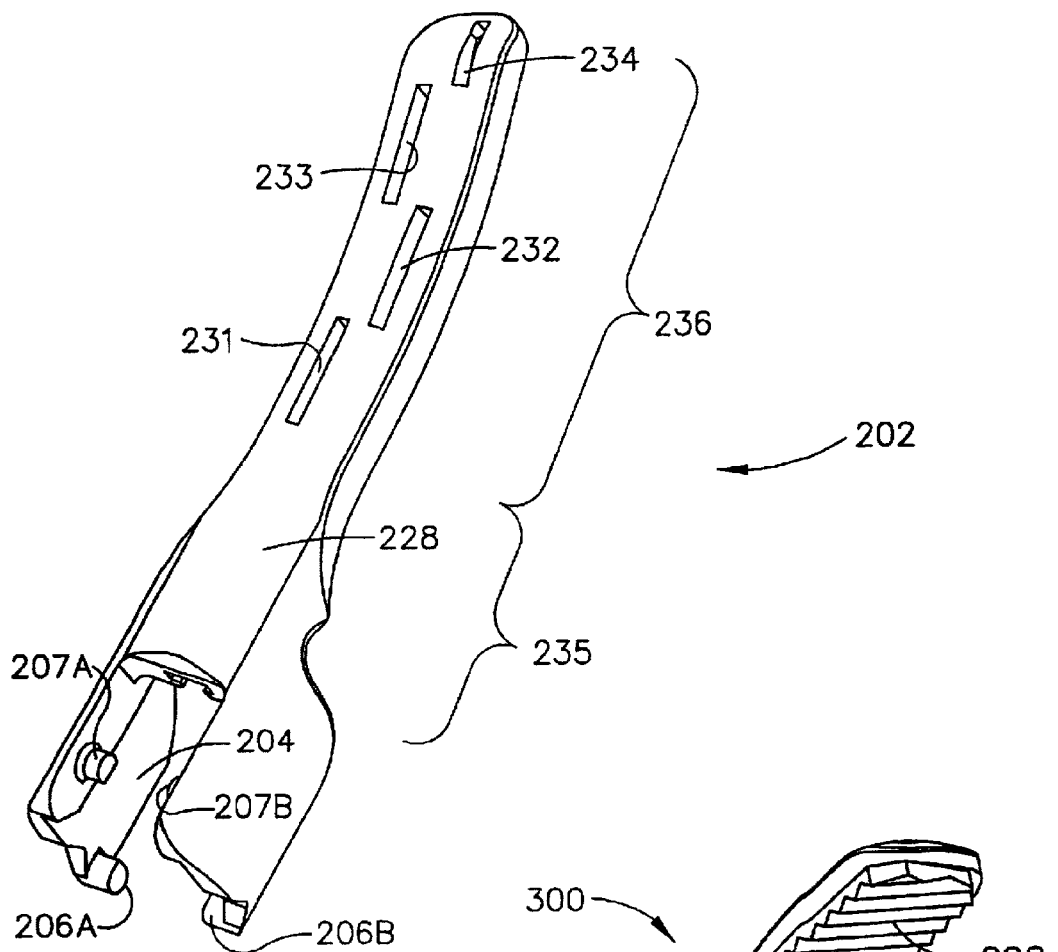
FIG. 24 is a top perspective view of a clamp arm of the camp coagulator.

Once the clamp coagulator 120 is attached to the acoustic assembly 80, the surgeon can rotate the rotational knob 190 to adjust the elongated member 150 at a desired angular position. As the rotational knob 190 is rotated, the teeth 269 of the tubular collar 260 slip over the pawls 286 of the yoke 280 into the adjacent notch or valley. As a result, the surgeon can position the end-effector 180 at a desired orientation. Rotational knob 190 may incorporate an indicator to indicate the rotational relationship between instrument housing 130 and clamp arm 202. As illustrated in FIGS. 17 and 18, one of the ridges 197 of rotational knob 190 may be used to indicate the rotational position of clamp arm 202 with respect to instrument housing 130 by utilizing, for example, an enlarged ridge 200. It is also contemplated that alternate indications such as the use of coloring, symbols, textures, or the like may also be used on rotational knob 190 to indicate position similarly to the use of enlarged ridge 200.

To detach the clamp coagulator 120 from the stud 50 of the acoustic assembly 80, the tool may be slipped over the elongated member 150 of the surgical tool 120 and rotated in the opposite direction, i.e., in a direction to unthread the ultrasonic waveguide 179 from the stud 50. When the tool is rotated, the hub 162 of the outer tube 160 allows torque to be applied to the ultrasonic waveguide 179 through the pin 163 to allow a relatively high disengaging torque to be applied to rotate the ultrasonic waveguide 179 in the unthreading direction. As a result, the ultrasonic waveguide 179 loosens from the stud 50. Once the ultrasonic waveguide 179 is removed from the stud 50, the entire clamp coagulator 120 may be thrown away.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. An ultrasonic surgical instrument comprising:
   an ultrasonic transmission member having a proximal end and a distal end;
   an ultrasonically actuated blade attached to the distal end of the transmission member, wherein the blade comprises:
      a distal end;
      a proximal end attached to the transmission member at a longitudinal vibratory node point;
      a curved treatment portion defining a plane of asymmetry and having an ultrasonically actuated motion in substantially a single plane; and
   a clamp member supported adjacent to the blade and having an open position in which at least a portion of the clamp member is spaced from the blade and a closed position in which the clamp member is adjacent to the blade and that the motion from the closed position to the open position occurs in a plane substantially perpendicular to the plane of motion of the blade.

2. The ultrasonic surgical instrument of claim 1, wherein the blade lies in a single plane perpendicular to the plane of asymmetry.

3. The ultrasonic surgical instrument of claim 1, wherein the curved treatment portion further comprises a balance asymmetry, wherein the balance asymmetry is positioned to counter torque created at the proximal end of the blade by the functional asymmetry.

4. The ultrasonic surgical instrument of claim 3, wherein the balance asymmetry is positioned such that transverse vibrations in at least one axis at the distal end of the blade are substantially equal to zero.

5. The ultrasonic surgical instrument of claim 3, wherein the balance asymmetry extends from the distal end of the blade to a point within the curved treatment portion.

6. The ultrasonic surgical instrument of claim 3, wherein the balance asymmetry extends from the distal end of the blade to a point proximal to the curved treatment portion.

7. An ultrasonic surgical instrument comprising a ultrasonic waveguide having a proximal end and a distal end, wherein the waveguide comprises:

a balanced ultrasonically actuated blade positioned at the distal end of the waveguide and having an ultrasonically actuated motion in substantially a single plane, wherein the blade comprises:

a distal end;

a proximal end;

a curved treatment portion comprising a balance portion including at least one balance asymmetry, wherein the balance asymmetry is positioned to counter torque created by the curved treatment portion; and a clamp member supported adjacent to the blade and having an open position in which at least a portion of the clamp member is spaced from the blade and a closed position in which the clamp member is adjacent to the blade and that the motion from the closed position to the open position occurs in a plane substantially perpendicular to the plane of motion of the blade.

8. An ultrasonic surgical instrument comprising:

a tubular sheath having a diameter, proximal end and a distal end;

an ultrasonic transmission member having a proximal end and a distal end positioned within the tubular sheath;

an ultrasonically actuated blade attached to the distal end of the transmission member and extending distally of the distal end of the tubular sheath, wherein the blade comprises:

a distal end;

a proximal end attached to the transmission member at a longitudinal vibratory node point;

a curved treatment portion defining a plane of asymmetry and having an ultrasonically actuated motion in substantially a single plane; and a clamp member configured to subscribe an arc larger than the diameter of the tubular shaft and supported adjacent to the blade and having an open position in which at least a portion of the clamp member is spaced from the blade and a closed position in which the clamp member is adjacent to the blade and that the motion from the closed position to the open position occurs in a plane substantially perpendicular to the plane of motion of the blade.

9. The ultrasonic surgical instrument of claim 8 further comprising a rotatable member operatively associated with the transmission member, the clamp member and the blade, the rotatable member being rotatable to cause corresponding rotation of the clamp member and the blade about a longitudinal axis of the instrument.

10. An ultrasonic surgical instrument of claim 8 further comprising a seal member positioned on the transmission member to dampen out unwanted torque generated by the functional asymmetry.

\* \* \* \* \*